United States Patent [19]

Cheronis et al.

[11] Patent Number: 5,635,593
[45] Date of Patent: Jun. 3, 1997

[54] BRADYKININ ANTAGONISTS

[75] Inventors: John C. Cheronis, Lakewood; James K. Blodgett, Broomfield; Eric T. Whalley, Golden; Shadrach R. Eubanks, Arvada; Lisa G. Allen, Parker, all of Colo.; Khe T. Nguyen, San Diego, Calif.

[73] Assignee: Cortech, Inc., Denver, Colo.

[21] Appl. No.: 440,352

[22] Filed: May 12, 1995

Related U.S. Application Data

[63] Continuation of Ser. No. 227,184, Apr. 13, 1994, which is a continuation of Ser. No. 859,582, Mar. 27, 1992, which is a continuation-in-part of Ser. No. 677,391, Apr. 1, 1991.

[51] Int. Cl.$^6$ .............................. C07K 7/18; A61K 38/00
[52] U.S. Cl. ..................... 530/314; 530/328; 530/402; 530/408; 530/807; 530/815; 530/816; 548/314.4; 548/521; 435/107; 435/117; 435/118; 435/121; 435/128; 435/129
[58] Field of Search ..................... 514/15, 12, 2; 530/314, 328, 402, 408, 807, 816, 815; 548/314.4, 521; 435/107, 118, 121, 117, 128, 129

[56] References Cited

U.S. PATENT DOCUMENTS

| | | | |
|---|---|---|---|
| 4,618,598 | 10/1986 | Conn | 514/6 |
| 4,894,443 | 1/1990 | Greenfield et al. | 530/388 |
| 5,416,191 | 5/1995 | Cheronis et al. | 530/314 |

FOREIGN PATENT DOCUMENTS 8901781   3/1989   WIPO.

OTHER PUBLICATIONS

Vaverk et al., 'Suyccinyl Bis–Bradykinins: Potent Agonists with Exceptional Resistance to Enzymatic Degradation', Peptide: Struc. and Func., Proceedings of the 8th Amer. Pept. Symp., Pierce Chem. Co., Rockford, IL, pp. 381–384 1983.

Stewart et al., "Bradyinin Chemistry: Agonists and Antagonist", Advances in Experimental Medicine and Biology, Plenum Press, NY, NY pp. 585–589 1983.

Calixto et al., 'Nonpeptide Bradykinin Antagonist', Bradykinin Antagonists: Basic and Clinical Research, Ronald Burch (Ed.), Marcel Dekker Inc., NY, NY, pp. 97–129 1991.

Stewart et al., "Bradykinin Chemistry: Agonists and Antagonist", Advances in Experimental Medicine and Biology; Plenum Press, NY, NY (1983) pp. 585–589.

Vavrek et al, "Succinyl Bis–Bradykinins:Potent Agonists with Except. Resist. to Enzymatic Degradation", Peptide: Struc. and Func, Proceedings of the 8th Amer. Peptide Symposium, Pierce Chem.Co, Rockford, IL (1983)pp. 381–384.

Bradykinin Antagonists: Basic and Clinical Research, Ronald Burch (Ed.), Marcel Dekker Inc., NY, NY, pp. 52–81.

*Primary Examiner*—Cecilia J. Tsang
*Assistant Examiner*—Anish Gupta
*Attorney, Agent, or Firm*—Cushman Darby Cushman IP Group of Pillsbury Madison & Sutro LLP

[57] ABSTRACT

A brandykinin antagonist of the formula:

$$X(BKA)_n$$

wherein BKA is the peptide chain of a bradykinin antagonist peptide, X is a linking group and n is a whole number greater than 1. The BKA substituents may be the same or different. Monomeric antagonists of the formula X(BKA) are also disclosed. Also disclosed are bradykinin antagonists of the formula:

$$(Y)(X)(BKA)$$

where X and BKA have the meanings indicated above and Y is the peptide chain of an antagonist or agonist for a non-bradykinin receptor.

12 Claims, 12 Drawing Sheets

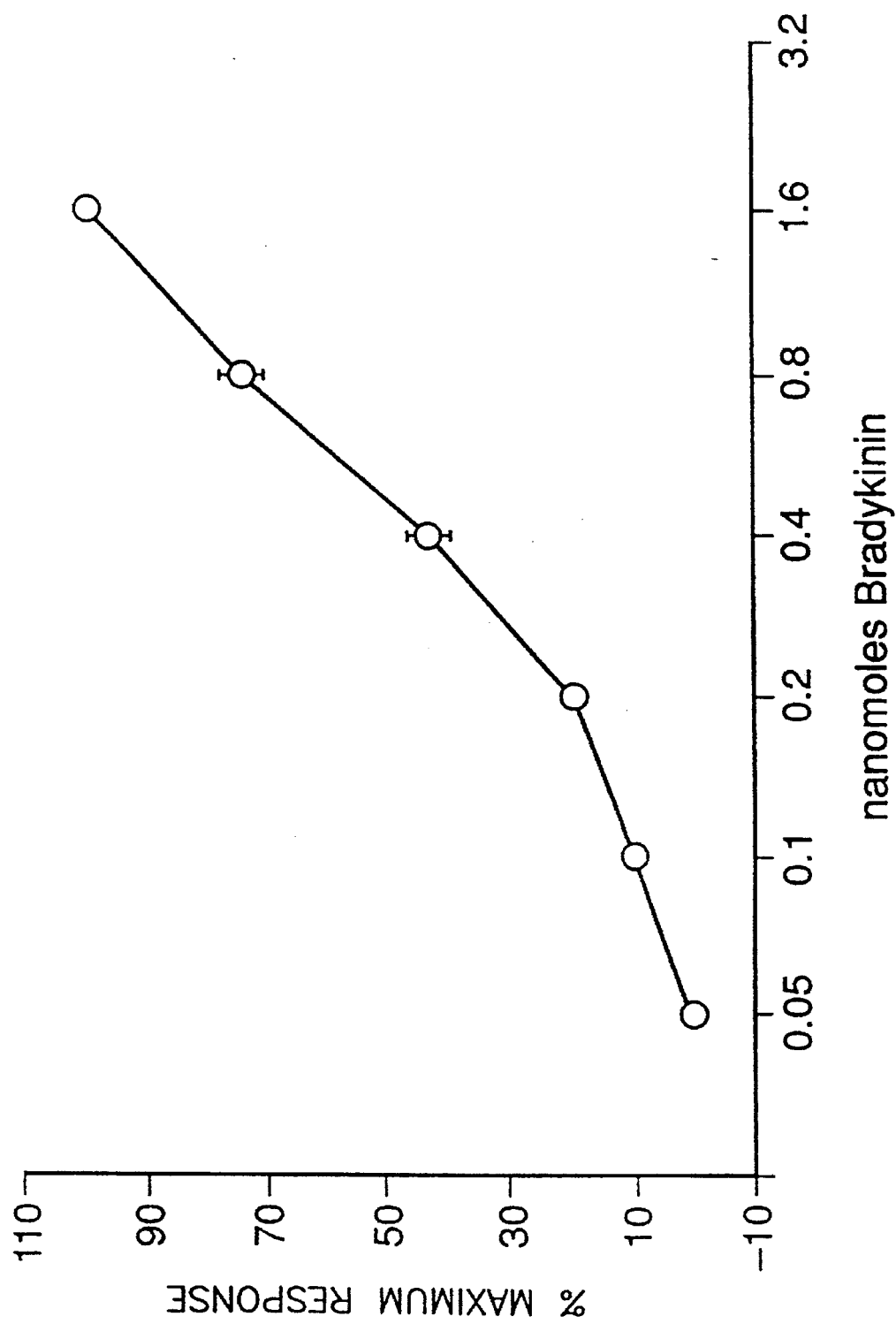

BRADYKININ ANTAGONISTS

This is a continuation of application Ser. No. 08/227,184, filed Apr. 13, 1994, which is a Rule 62 FWC of Ser. No. 07/859,582 filed Mar. 27, 1992, which is a CIP of Ser. No. 07/677,391 filed Apr. 1, 1991.

The present invention relates to bradykinin antagonists.

BACKGROUND OF THE INVENTION

Bradykinin (BK) is a peptide composed of nine amino acids ($Arg^1$-$Pro^2$-$Pro^3$-$Gly^4$-$Phe^5$-$Ser^6$-$Pro^7$-$Phe^8$-$Arg^9$) which, along with lysyl-BK (kallidin), is released from precursor kininogens by proteases termed kallikreins. Plasma kallikrein circulates as an inactive zymogen from which active kallikrein is released by Hageman factor. Tissue kallikrein appears to be located predominantly on the outer surface of epithelial cell membranes at sites thought to be involved in transcellular electrolyte transport.

Two major kinin precursor proteins, high molecular weight and low molecular weight kininogen, are synthesized in the liver, circulate in plasma, and are found in secretions such as urine and nasal fluid. High molecular weight kininogen is cleaved by plasma kallikrein, yielding BK, or by tissue kallikrein, yielding kallidin. Low molecular weight kininogen, however, is a substrate only for tissue kallikrein. In addition, some conversion of kallidin to BK may occur inasmuch as the amino terminal lysine residue of kallidin is removed by plasma aminopeptidases. Plasma half-lives for kinins are approximately 15 sec., with a single passage through the pulmonary vascular bed resulting in 80-90% destruction. The principle catabolic enzyme in vascular beds is the dipeptidyl carboxypeptidase kininase II or angiotensin-converting enzyme (ACE). A slower acting enzyme, kininase I, or carboxypeptidase N, which removes the carboxyl terminal Arg, circulates in plasma in great abundance. This suggests that it may be the more important catabolic enzyme physiologically. Des-$Arg^9$-bradykinin as well as des-$Arg^{10}$-kallidin formed by kininase I acting on BK or kallidin, respectively, are acting $BK_1$ receptor agonists, but are relatively inactive at the more abundant $BK_2$ receptor at which both BK and kallidin are potent agonists.

Bradykinin is known to be one of the most potent naturally occurring stimulators of C-fiber afferents mediating pain. It also is a potent vasodilator, edema-producing agent, and stimulator of various vascular and non-vascular smooth muscles in tissues such as uterus, gut and bronchiole. The kinin/kininogen activation pathway has also been described as playing a pivotal role in a variety of physiologic and pathophysiologic processes, being one of the first systems to be activated in the inflammatory response and one of the most potent stimulators of: (i) phospholipase $A_2$ and, hence, the generation of prostaglandins and leukotrienes; and (ii) phospholipase C and thus, the release of inositol phosphates and diacylglycerol. These effects are mediated predominantly via activation of BK receptors of the $BK_2$ type.

Direct application of bradykinin to denuded skin or intra-arterial or visceral injection results in the sensation of pain in animals and in man. Kinin-like materials have been isolated from inflammatory sites produced by a variety of stimuli. In addition, bradykinin receptors have been localized to nociceptive peripheral nerve pathways and BK has been demonstrated to stimulate central fibers mediating pain sensation. Bradykinin has also been shown to be capable of causing hyperalgesia in animal models of pain. (See, Burch et al, "Bradykinin Receptor Antagonists", *J. Med. Chem.*, 30:237–269 (1990) and Clark, W. G. "Kinins and the Peripheral and Central Nervous Systems", *Handbook of Experimental Pharmacology*, Vol. XXV: Bradykinin, kallidin, and kallikrein. Erdo, E. G. (ed.), 311–322 (1979)) .

These observations have led to considerable attention being focused on the use of BK antagonists as analgesics. A number of studies have demonstrated that bradykinin antagonists are capable of blocking or ameliorating both pain as well as hyperalgesia in both animals and man. See, Ammons, W. S. et al, "Effects of intracardiac bradykinin on $T_2$-$T_5$ medial spinothalamic cells", *The American Physiological Society*, 0363-6119 (1985); Clark, W. G., "Kinins and the Peripheral and Central Nervous Systems", *Handbook of Experimental Pharmacology*, Vol. XXV: Bradykinin, kallidin, and kallikrein. Erdo, E. G. (ed.), 311–322 (1979); Costello, A. H. et al, "Suppression of carrageenan-induced hyperalgesia, hyperthermia and edema by a bradykinin antagonist", *European Journal of Pharmacology*, 171:259–263 (1989); Laneuville et al, "Bradykinin analogue blocks bradykinin-induced inhibition of a spinal nociceptive reflex in the rat", *European Journal of Pharmacology*, 137:281–285 (1987); Steranka et al, "Antinociceptive effects of bradykinin antagonists", *European Journal of Pharmacology*, 16:261–262 (1987); Steranka et al, "Bradykinin as a pain mediator:Receptors are localized to sensory neurons, and antagonists have analgesic actions", *Neurobiology*, 85:3245–3249 (1987).

Currently accepted therapeutic approaches to analgesia have significant limitations. While mild to moderate pain can be alleviated with the use of nonsteroidal anti-inflammatory drugs and other mild analgesics, severe pain such as that accompanying surgical procedures, burns and severe trauma requires the use of narcotic analgesics. These drugs carry the limitations of abuse potential, physical and psychological dependence, altered mental status and respiratory depression which significantly limit their usefulness.

Prior efforts in the field of BK antagonists indicate that such antagonists can be useful in a variety of roles. These include use in the treatment of burns, perioperative pain, migraine and other forms of pain, shock, central nervous system injury, asthma, rhinitis, premature labor, inflammatory arthritis, inflammatory bowel disease, etc.

For example, Whalley et al, in *Naunyn Schmiederberg's Arch. Pharmacol.*, 336:652–655 (1987) have demonstrated that BK antagonists are capable of blocking BK-induced pain in a human blister base model. This suggests that topical application of such antagonists would be capable of inhibiting pain in burned skin, e.g. in severely burned patients in whom large doses of narcotics are required over long periods of time and for the local treatment of relatively minor burns or other forms of local skin injury.

The management of perioperative pain requires the use of adequate doses of narcotic analgesics to alleviate pain while not inducing excessive respiratory depression. Post-operative narcotic-induced hypoventilation predisposes patients to collapse of segments of the lungs, a common cause of post-operative fever, and frequently delays discontinuation of mechanical ventilation. The availability of a potent non-narcotic parenteral analgesic could be a significant addition to the treatment of perioperative pain. While no currently available BK antagonist has the appropriate pharmacodynamic profile to be used for the management of chronic pain, frequent dosing and continuous infusions are already commonly used by anesthesiologists and surgeons in the management of perioperative pain.

Several lines of evidence suggest that the kallikrein/kinin pathway may be involved in the initiation or amplification of vascular reactivity and sterile inflammation in migraine. (See, Back et al, "Determination of components of the kallikrein-kinin system in the cerebrospinal fluid of patients with various diseases", Res. Clin. Stud. Headaches, 3:219–226 (1972)). Because of the limited success of both prophylactic and non-narcotic therapeutic regimens for migraine as well as the potential for narcotic dependence in these patients, the use of BK antagonists offers a highly desirable alternative approach to the therapy of migraine.

Bradykinin is produced during tissue injury and can be found in coronary sinus blood after experimental occlusion of the coronary arteries. In addition, when directly injected into the peritoneal cavity, BK produces a visceral type of pain. (See, Ness et al, "Visceral pain: a review of experimental studies", Pain, 41:167–234 (1990)). While multiple other mediators are clearly involved in the production of pain and hyperalgesia in settings other than those described above, it is also believed that antagonists of BK have a place in the alleviation of such forms of pain as well.

Shock related to bacterial infections is a major health problem. It is estimated that 400,000 cases of bacterial sepsis occur in the United States yearly; of those 200,000 progress to shock, and 50% of these patients die. Current therapy is supportive, with some suggestion in recent studies that monoclonal antibodies to Gram-negative endotoxin may have a positive effect on disease outcome. Mortality is still high, even in the face of this specific therapy, and a significant percentage of patients with sepsis are infected with Gram-positive organisms which would not be amenable to anti-endotoxin therapy.

Multiple studies have suggested a role for the kallikrein/kinin system in the production of shock associated with endotoxin. See, Aasen et al, "Plasma Kallikrein Activity and Prekallikrein Levels during Endotoxin Shock in Dogs", Eur. Surg., 10:50–62 (1977); Aasen et al, "Plasma Kallikrein-Kinin System in Septicemia", Arch. Surg., 118:343–346 (1983); Katori et al, "Evidence for the involvement of a plasma kallikrein/kinin system in the immediate hypotension produced by endotoxin in anaesthetized rats", Br. J. Pharmacol., 98:1383–1391 (1989); and Marceau et al, "Pharmacology of Kinins: Their Relevance to Tissue Injury and Inflammation", Gen. Pharmacol., 14:209–229 (1982). Recent studies using newly available BK antagonists have demonstrated in animal models that these compounds can profoundly affect the progress of endotoxic shock. (See, Weipert, et al., "Attenuation of Arterial Blood Pressure Fall in Endotoxic Shock in the Rat Using the Competitive Bradykinin Antagonist Lys-Lys-[Hyp$^2$, Thi$^{5,8}$, D-Phe$^7$]-BK", Brit J. Pharm., 94, 282–284,(1988)). Less data is available regarding the role of BK and other mediators in the production of septic shock due to Gram-positive organisms. However, it appears likely that similar mechanisms are involved. Shock secondary to trauma, while frequently due to blood loss, is also accompanied by activation of the kallikrein/kinin system. (See, Haberland, "The Role of Kininogenases, Kinin Formation and Kininogenase Inhibitor in Post Traumatic shock and Related Conditions", Klinische Woochen-schrift, 56:325–331 (1978)).

Numerous studies have also demonstrated significant levels of activity of the kallikrein/kinin system in the brain. Both kallikrein and BK dilate cerebral vessels in animal models of CNS injury. (See, Ellis et al, "Inhibition of Bradykinin- and Kallikrein-Induced Cerebral Arteriolar Dilation by Specific Bradykinin Antagonist", Stroke, 18:792–795 (1987) and Kamitani et al, "Evidence for a Possible Role of the Brain Kallikrein-Kinin System in the Modulation of the Cerbral Circulation", Circ. Res., 57:545–552 (1985)). Bradykinin antagonists have also been shown to reduce cerebral edema in animals after brain trauma. Based on these data, it is believed that BK antagonists should be useful in the management of stroke and head trauma.

Other studies have demonstrated that BK receptors are present in the lung, that BK can cause bronchoconstriction in both animals and man and that a heightened sensitivity to the bronchoconstrictive effect of BK is present in asthmatics. Some studies have been able to demonstrate inhibition of both BK and allergen-induced bronchoconstriction in animal models using BK antagonists. These studies indicate a potential role for the use of BK antagonists as clinical agents in the treatment of asthma. (See, Barnes, "Inflammatory Mediator Receptors and Asthma", Am. Rev. Respir. Dis., 135:S26-S31 (1987); Burch et al, "Bradykinin Receptor Antagonists", J. Med. Chem., 30:237–269 (1990); Fuller et al, "Bradykinin-induced bronchoconstriction in Humans", Am. Rev. Respir. Dis., 135:176–180 (1987); Jin et al, "Inhibition of bradykinin-induced bronchoconstriction in the guinea-pig by a synthetic $B_2$ receptor antagonist", Br. J. Pharmacol., 97:598–602 (1989) and Polosa et al, "Contribution of histamine and prostanoids to bronchoconstriction provoked by inhaled bradykinin in atopic asthma", Allergy, 45:174–182 (1990)). Bradykinin has also been implicated in the production of symptoms in both allergic and viral rhinitis. These studies include the demonstration of both kallikrein and BK in nasal lavage fluids and that levels of these substances correlate well with symptoms of rhinitis. (See, Baumgarten et al, "Concentrations of Glandular Kallikrein in Human Nasal Secretions Increase During Experimentally Induced Allergic Rhinitis", J. Immunology, 137:1323–1328 (1986); Jin et al, "Inhibition of bradykinin-induced bronchoconstriction in the guinea-pig by a synthetic $B_2$ receptor antagonist", Br. J. Pharmacol., 97:598–602 (1989) and Proud et al, "Nasal Provocation with Bradykinin induces Symptoms of Rhinitis and a Sore Throat", Am. Rev. Respir Dis, 137:613–616 (1988)).

In addition, studies have demonstrated that BK itself can cause symptoms of rhinitis.

Stewart and Vavrek in "Chemistry of Peptide Bradykinin Antagonists", Bradykinin Antagonists: Basic and Chemical Research, R. M. Burch (Ed.), pages 51–96 (1991) discuss peptide BK antagonists and their possible use against effects of BK. A great deal of research effort has been expended towards developing such antagonists with improved properties. However, notwithstanding extensive efforts to find such improved BK antagonists, there still remains a need for more effective BK antagonists.

The two major problems with presently available BK antagonists are their low levels of potency and their extremely short durations of activity. Accordingly, important objectives of the present invention include the provision of novel BK antagonist peptides which are characterized by increased potency and duration of action. Other objectives will also be hereinafter evident.

SUMMARY OF THE INVENTION

The invention is based, in one important embodiment, on the finding that compounds comprising two or more bradykinin antagonist (BKA) peptides which are chemically linked together to form a dimer or higher oligomer ("mer") demonstrate greater potency and/or duration of action than the parent bradykinin antagonist peptide itself.

Broadly speaking, the compounds of the invention, according to this embodiment, can be illustrated by the formula:

$$X(BKA)_n \quad (I)$$

where BKA is the nucleus of any bradykinin antagonist peptide, X is a linking group and n is a whole number greater than 1. Preferably n is 2, thereby providing a dimer. However, the compound may include more than two BKA substituents, i.e. the compound may be a trimer or even a higher "mer", up to the limit permitted by the nature of the linking group.

The BKA substituents may be the same throughout so as to provide, in a sense, a homogenous compound. On the other hand, it may be preferred in some situations that the compound include different substituents, i.e. the compound may be heterogeneous with respect to the BKA substituents or may contain one or more BKAs and a ligand or ligands of a different nature. Both homogenous and heterogenous embodiments are contemplated by the present invention as discussed more fully below.

The concept of providing dimers of pharmaceutically active materials to improve such characteristics as metabolic stability, selectivity and receptor binding has previously been described for other systems. This prior work has included the dimerization of peptide agonists and antagonists in order to increase potency and/or duration of action. (See, Caporale et al, *Proc. 10th American Peptide Sym.*, Pierce Chemical Co., Rockford, Ill. 449–451 (1988) and Rosenblatt et al, European Patent Application No. EP 293130A2). Thus, dimerization of peptide agonists has been disclosed for enkephalins/endorphins (Shimohigashi, Y. et al, *BBRC*, 146, 1109–1115, 1987); substance P (Higuchi, Y., et al, *E.J.P.*, 160, 413–416, 1989); bradykinin (Vavrek, R. and Stewart, J., *J. Proc. 8th Amer. Pept. Symp.*, 381–384, 1983); neurokinin A & B, (Kodama, H., et al, *E.J.P.*, 151, 317–320, 1988); insulin (Roth, R. A., et al, *FEBS*, 170, 360–364, 1984) and atrial natriuretic peptide (Chino, N., et al, *BBRC*, 141, 665–672, 1986). Dimerization of antagonists has been shown for parathyroid hormone (Caproale, L. H., et al, *Proc. 10th Amer. Pept. Symp.*, 449–451, 1987)). However, the literature has not disclosed BK antagonist dimers or higher "mers" as contemplated herein.

Furthermore, prior dimerization efforts have, in large measure, favored dimerizing from one or both ends of the present compounds whereas, it has been found, as part of the present invention, that dimerizing various BK antagonists from an external position using either the free alpha amino or carboxyl groups at the termini of these ligands does not appear to enhance, and in most cases reduces, the activity of these agents. Accordingly, the invention contemplates, as a preferred embodiment, linking the BKA peptide ligands at a position intermediate to the ends of the peptide involved.

A further embodiment of the invention provides a novel group of "monomeric" compounds of the formula:

$$X(BKA) \quad (II)$$

i.e. compounds of formula (I) where n is 1 and the modifier X functions to improve the antagonist properties of the parent BKA peptide represented by the BKA substituent. This improvement may be shown by, for example, increased potency and/or duration of action. Here again, the modifier X is advantageously positioned within the peptide chain, i.e., not at a terminal end thereof.

In another embodiment, the invention contemplates dimers of the formula:

$$(Y)(X)(BKA) \quad (III)$$

where X and BKA have the meanings indicated above and Y is a ligand which demonstrates antagonist or agonist activity for a non-bradykinin receptor.

Thus, in brief, the invention is concerned with (a) bradykinin antagonist peptides of formula (I), which may be homogeneous or heterogeneous dimers or higher "mers", (b) monomers of the formula (II) where a BKA is modified to include the group X and (c) heterodimers of formula (III) demonstrating both bradykinin antagonist activity and non-BK receptor activity (antagonist or agonist).

BRIEF DESCRIPTION OF THE FIGURES

FIG. 5A. Rat blood pressure dose response curve (n=10), Dose response curve to BK in the anaesthetized rat, From this an $ED_{50}$ was chosen: 0.4 nmoles. Vertical bars represent standard errors of the means of n=10.

DETAILED DESCRIPTION OF THE INVENTION

Figure 1A:
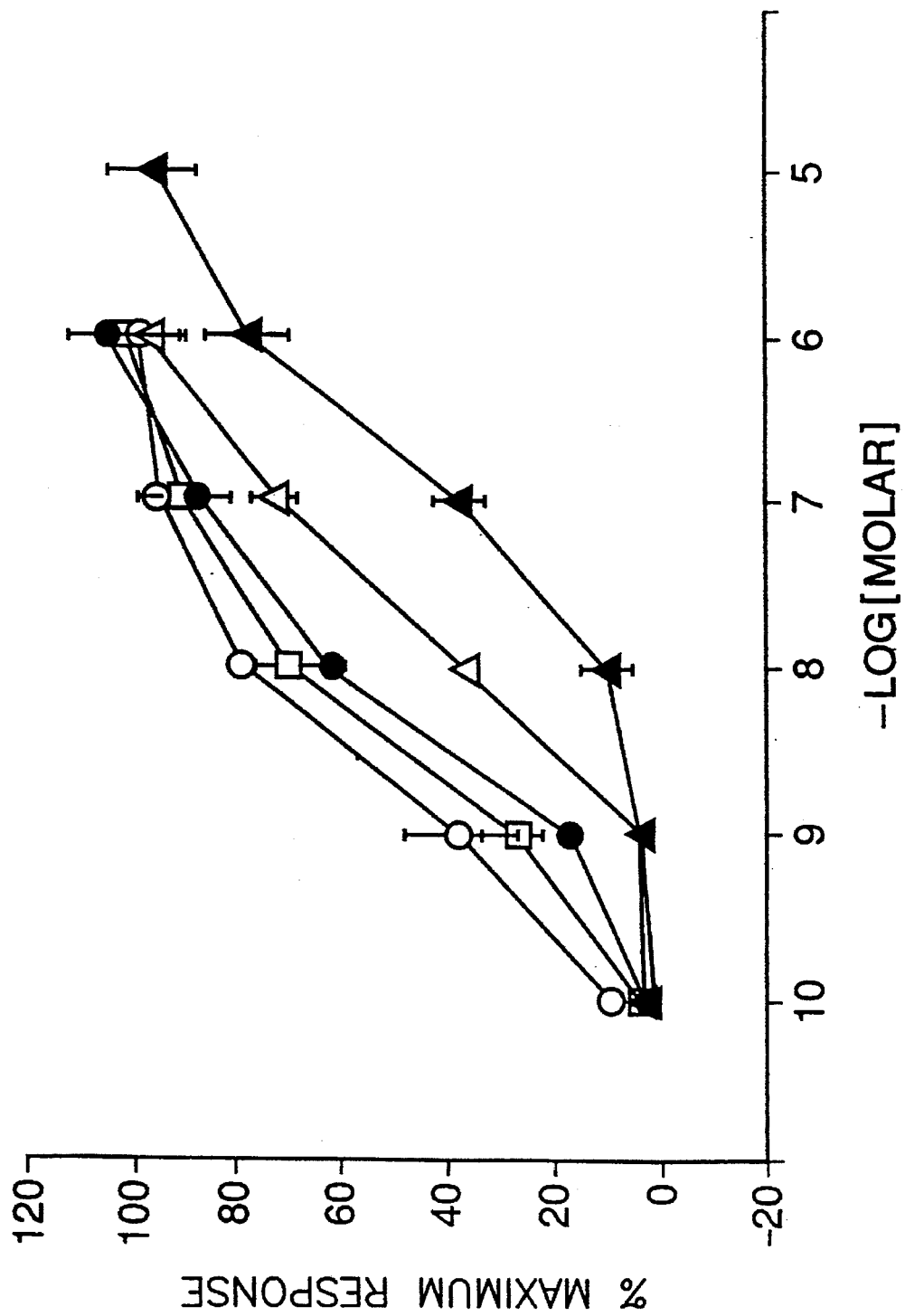
FIG. 1A. Concentration-effect curves to BK in the absence and presence of CP-0126 on rat uterus in vitro. Vertical bars represent standard errors of the means of n=3–4. Note full recovery of the BK Curve following a 40 minute washing-off period of the antagonist. (Open circles are BK, N=4; filled circles are CP0126–7M; open triangles are CP0126–6M; filled triangles are CP0126–5M; and open squares are BK REC; $pA_2$=7.1.)

Numerous BK antagonist peptides are known in the art and any of these may be used for present purposes to provide the BK substituents. One of the most potent BKAs in vitro is the peptide having the formula:

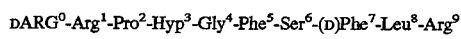

$DARG^0$-$Arg^1$-$Pro^2$-$Hyp^3$-$Gly^4$-$Phe^5$-$Ser^6$-$(D)Phe^7$-$Leu^8$-$Arg^9$ (See, Regoli et al, Trends in Pharmacological Science, 11:156–161 (1990)). This peptide is referred to herein for convenience as CP-0088 and, for purposes of the present invention, it may be used for linking with either the same or a different peptide having BKA activity to provide antagonists as represented by formula (I).

While CP-0088 is used herein to illustrate various aspects of the invention, it needs to be emphasized that the invention contemplates the use of any available or known BK antagonist peptide for present purposes. For example, a wide variety of modifications have been proposed for BK antagonist peptides in the recent patent literature and these can be used to provide the BKA component or components of the present products. (See, for example, EP-A-0334244 (Procter and Gamble) which discloses nona- and larger BK antagonist peptides in which certain amino acid residues are modified). EP-A-0370453 (Hoechst) and WO 89/01780 and WO 89/01781 (Stewart et al) also describe BK antagonist peptides. None of these patent publications appears to show homogeneous or heterogenous dimers or higher "mers", or the linker modified monomers as contemplated herein. However, as noted, the peptides of these publications can be used in the practice of the present invention. Accordingly, while CP-0088 is used for purposes of illustration, the invention is not to be viewed as limited thereto.

According to one embodiment of the invention, the linker X is advantageously joined to the parent peptide antagonist through a cysteine (Cys) residue within the peptide chain. This may require initially modifying the starting peptide so that it includes a Cys residue in the appropriate position within the peptide chain.

The invention is illustrated using various Cys derivatives of CP-0088 where Cys replaces Set or some other amino acid in the CP-0088 peptide chain. It has been found that Cys conveniently provides for covalent attachment to an appropriate linker X through its reactive sulfhydryl group producing a stable thioether bond. According to this aspect of the invention, it is preferred to incorporate the cysteine residue at the "6" position of CP-0088. This position has been previously regarded as relatively unimportant. (See, Stewart, J. M. and Vavrek, R. J., (1991), "Chemistry of peptide bradykinin antagonists", in Bradykinin Antagonists: Basic and Clinical Research, R. M. Burch Marcel Dekkar Inc. N.Y., pp. 51–96.) However, an important aspect of the present invention is based on the finding that, in contrast to this generally accepted view of the 6 position, this specific locus is important for both dimerization and monomer modification in providing optimal properties for the resulting products. It will, however, be appreciated that the invention is not limited to modifications in the "6" position.

As shown hereinafter, any one of a wide variety of linkers X may be used for present purposes. This group functions to chemically join together two or more peptides one or both of which are BKAs. This may be the only function of the linker. However, the linker can itself also contribute to improve the overall antagonist properties as shown hereinafter. Preferably the linker is a flexible, linear group which is readily reactive with the desired ligands. Preferred linkers include bismaleimidoalkanes (BMAs) such as bismaleimidohexane (BMH). Reactions with such a linker occur between its maleimido groups and the sulfhydryl moiety of a cysteine residue within the peptide chain to provide an S-succinimido derivative. For example, a 1,6-bis-S-succinimidohexane (BSH) dimer can be prepared by reacting 2 equivalents of Cys-containing peptide antagonist and 1 equivalent of bismaleimidohexane (BMH). Other suitable linking groups X are described later.

One of the preferred dimer antagonists of formula (I) according to the invention is identified herein, for ease of reference, as CP-0127. This compound has been found to have significantly greater potency and half-life than most of the presently known BKAs, including CP-0088 which, as noted earlier, is considered to be one of the more potent BK antagonists known in the art. The improved antagonist properties of CP-0127 are quite unexpected in that they represent more than what might be thought of as the normal additive effect of combining two or more peptide antagonists.

Compound CP-0127, which demonstrates all the characteristics required for pharmaceutical application as a BKA, e.g. the compound is suitable for parenteral use in the treatment of acute indications such as septic shock and perioperative pain, may be structurally illustrated as follows:

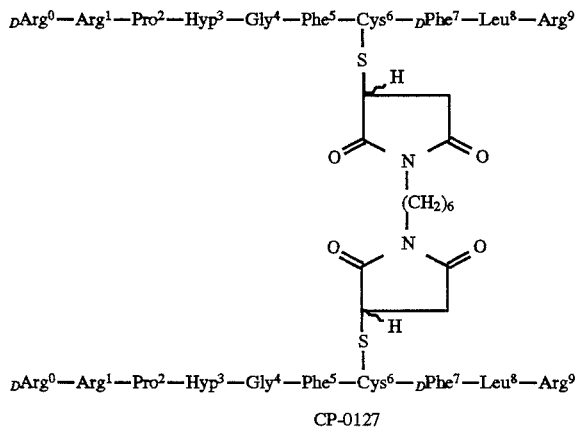

CP-0127

As will be evident, CP-0127 is a homogeneous dimer in the sense that the two peptide chains attached to the linker are the same. The compound consists of two equivalents of the $Cys^6$ derivative of the BKA CP-0088, i.e., CP-0088 where Ser in the "6" position has been replaced by cysteine (Cys), covalently joined together by reaction between the sulfhydryl moiety of Cys and bismaleimidohexane (BMH). The resultant product is a 1,6-bis-S-succinimidohexane (BSH) dimer of $Cys^6$ CP-0088.

The cysteine derivative ($Cys^6$) of CP-0088 can be prepared by conventional means. This $Cys^6$ derivative, which is identified herein as CP-0126 for ease of reference, may then be reacted with the desired bismaleimido reagent. In the case of CP-0127, where the bismaleimido reagent is bismaleimidohexane (BMH), the dimer (CP-0127) is obtained according to the following reaction scheme:

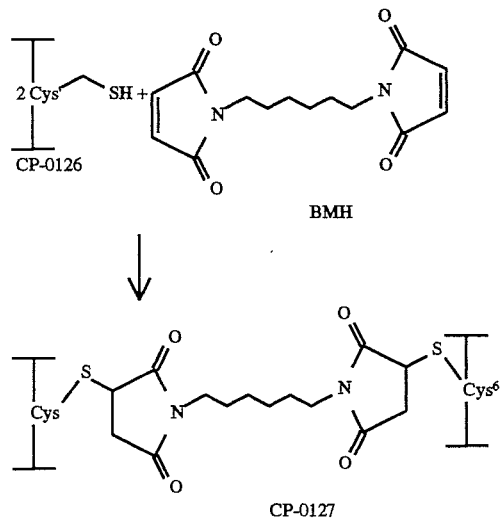

The foregoing illustrates only one possible way of preparing the products of formula (I). In an alternative method, the linker may be joined to a fragment of the BKA peptide, another peptide fragment joined to the other end of the linker and the balance of the respective peptides (BKA) completed by adding whatever other peptide fragments might be required. Those skilled in the art will recognize that whatever process steps are used, precautions need to be taken to protect various functional groups, notably amino and carboxy termini of the peptides or fragments thereof, from undesired reaction.

While BMH provides a preferred linking group X, other bismaleimide alkanes (BMA), for example, any bismaleimido reagents where the alkane contains from 1–12 carbons or more, may be used. The alkane group may also be substituted or interrupted by, for example, carbonyl and/or amino groups. While the length and nature of the alkyl chain in the BMA may be varied as noted, it appears that, as the length increases from 1–12 carbons, the $pA_2$ does not vary substantially. However, the inhibition of recovery increases. Additionally, as the alkyl chain length increases beyond 8 carbon atoms, partial agonism may be noted. Generally speaking, when using a BMA linker with CP-0126 as the BK component, the highest $pA_2$ values are obtained with alkyl chain lengths in the range of 6 to 9 carbon atoms and it appears that, of such linkers, the best results are obtained using BMH (bismaleimidohexane) to provide the indicated BSH linkage. However, as indicated, effective results can be obtained using other types of linkers. Thus, it is not essential that the group X include the succinimido sUbstituent provided the modification used is effective to link together the BKA peptide substituents without undesirably affecting the antagonist properties.

Representative alternatives to BMH as the linking group are shown below with the resulting dimer designation, as used later herein, shown to the left of the linker structure, it being understood that, in each instance, the BKA component of the dimer/trimer is the same as in CP-0126.

| DIMER/TRIMER | LINKER |
|---|---|
| CP-0162 | 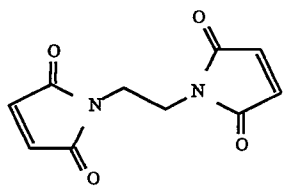 |
| CP-0163 | 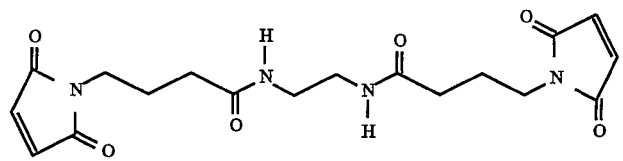 |
| CP-0164 | 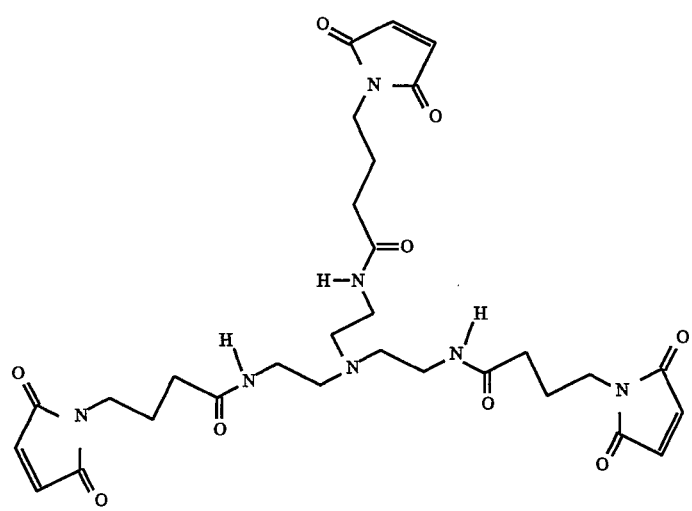 |
| CP-0165 | 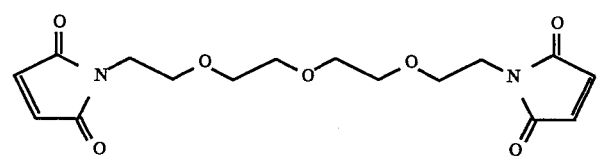 |
| CP-0166 | 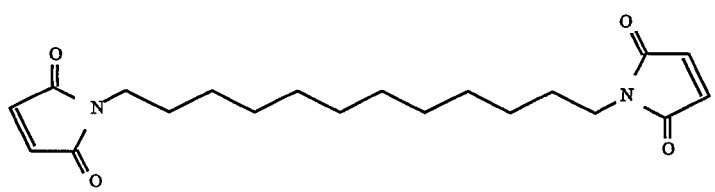 |
| CP-0170 | 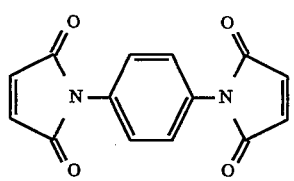 |
| CP-172 | 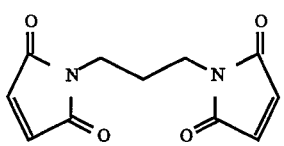 |

| DIMER/TRIMER | LINKER |
|---|---|
| CP-0176 | 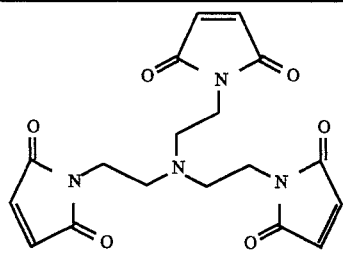 |
| CP-0177 | 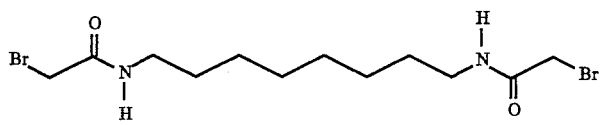 |

As will be evident, the invention contemplates the use of a wide variety of linkers X, with or without Cys-modification of the parent BK antagonist peptide (BKA). A further alternative to linkers of the type referred to above, which makes it possible to avoid the cysteine modification as described for the BSH type of compounds described earlier, is shown below:

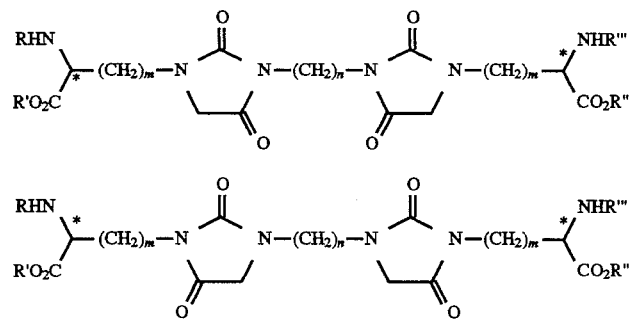

n = 2–12
m = 1–12
*Chirality can be equivalent to either "D" or "L" amino acids

R/R''' can be any combination of protecting groups such as N-t-Boc, Fmoc, Npys

R'/R'' can be any combination of protecting groups such as a methyl ester, ethyl ester or benzyl ester, the protecting groups R, R', R'' and R''' being such that they can be differentially removed in order to covalently attach peptide fragments as necessary to make, for example, an effective $BK_1$, $BK_2$, $NK_1$, $NK_2$ receptor antagonist or a μ opioid receptor agonist.

The general syntheses of the linkers of type I and II may be carried out in the following manner. Several separate fragments consisting of organic linkers and properly protected amino acids are prepared and joined together. The resulting fragments are then cyclized intramolecularly to the general hydantoin structures using the condition of base catalyzed cyclization.

More specifically, the synthesis of type I linker involves the preparation of the following separate fragments:

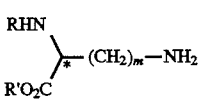 (1)

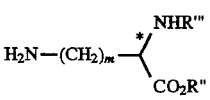 (2)

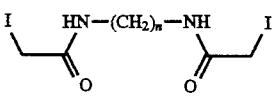 (3)

Fragments (1), (2) and (3) are joined together to form:

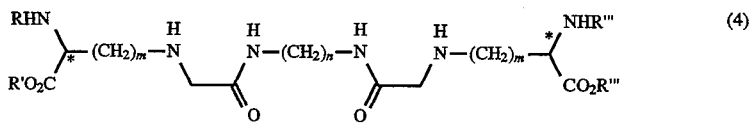

Fragment (4) is then treated with ethyl chloroformate followed by base-catalyzed cyclization conditions to yield the desired type I alternative linker.

The synthesis of type II linker involves the preparation of the following separate fragments:

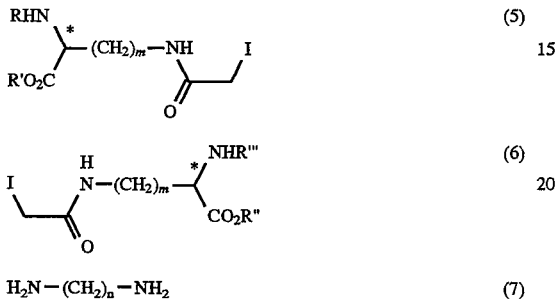

Fragments (5), (6) and (7) are joined to form:

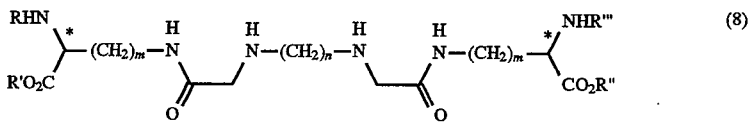

Fragment (8) is then treated with ethyl chloroformate followed by base catalyzed cyclization conditions to yield the desired type II alternative linker.

Once synthesized, the desired linkers from either Group I or II can be condensed with the appropriate peptide fragments to form the desired hetero- or homo-dimer. Illustrated below is a schematic representation of such a synthesis:

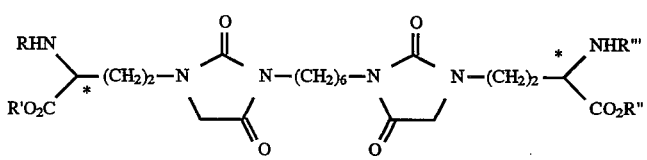

* = "L" Amino Acid Chirality

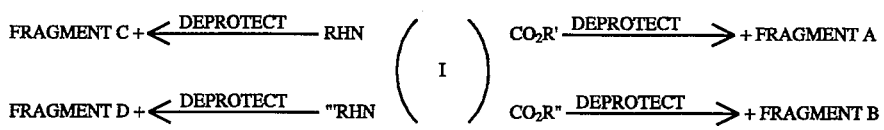

EXAMPLE:  R' = Methyl or Ethyl Ester
R" = Benzyl Ester
R = 3-Nitropyridyl sulfide ($N_{PYS}$)
R''' = FMOC FRAGMENT:  A = $NH_2$—Pro—Leu
B = $NH_2$—DPhe—Leu—Arg
C = Lys—Arg—Pro—Pro—Gly—Phe—$CO_2H$
D = DArg—Arg—Pro—Hyp—Gly—Phe—$CO_2H$

FINAL PRODUCT:

-continued

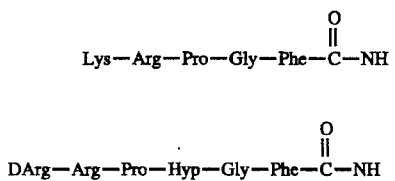 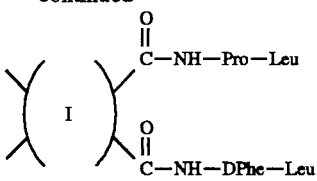

```
Lys—Arg—Pro—Gly—Phe—C(=O)—NH                    C(=O)—NH—Pro—Leu       BK₁ Selective
                                      \       /                        Antagonist
                                       \     /
                                        \ I /
                                        / | \
                                       /     \
DArg—Arg—Pro—Hyp—Gly—Phe—C(=O)—NH                C(=O)—NH—DPhe—Leu—Arg  BK₂ Selective
                                                                        Antagonist
```

The above synthesis illustrates the production of a heterodimer wherein each of the reactive groups of the linker are capable of being differentially deprotected so that all four fragments of the heterodimer can be added separately.

It will be appreciated that the type of linker shown above permits "offsetting" the ligands, i.e. differentially coupling them to the linker. For example, it is possible to make a ligand that is linked from the "6" position on one side and the "5" position on the other if this is deemed desirable for pharmacological reasons. An example of this type of preferred heterodimer is the $BK_2$ antagonist/$NK_1$ antagonist heterodimer exemplified later herein wherein positions 4, 5 and 6 in the $NK_1$ antagonist ligand are preferred. Alternatively, the μ-opioid agonists, also discussed later in connection with the Formula (III) components, can utilize this type of linker except that only one fragment needs to be coupled to the linker since coupling from the C-terminus is the preferred synthesis strategy for these types of heterodimers.

It will be recognized from the foregoing that the compounds of formulas (I)–(II) according to the invention may be prepared using readily available procedures. The antagonist peptide portions are readily available or may be prepared in fragments using solid or solution-phase peptide synthesis techniques. Known procedures may be used to provide a Cys residue in the desired position within the peptide chain and conventional chemistry is involved in adding the linker modification and in any subseguent-"mer" formation.

The invention is illustrated in the following examples and the related FIGS. 1A, 1B, 2A, 2B, 2C, 3, 4, 5A, 5B, 6, 7 and 8(a)–8(c), which demonstrate various aspects of the invention.

EXAMPLE 1

Preparation of CP-0127

The peptide, CP-0126, which in dimerized bismaleimidohexane (BMH) to produce CP-0127 was generated by solid phase peptide synthesis using a standard stepwise elongation of the peptide chain common in the peptide field (J. M. Stewart and J. D. Young, *Solid Phase Peptide Synthesis*, Pierce Chemical Co., 1984). Briefly stated, solid phase peptide synthesis begins with $N^\alpha$-deprotection of the amino acid attached to the synthesis resin. This step is followed by neutralization and washing of the deprotected amino acid-containing resin which prepares it to react with the next amino acid, itself activated by dicyclohexylcarbodiimide and 1-hydroxybenzotriazole to facilitate the formation of the first peptide bond (—CO—NH—). A subsequent washing of the now (di)peptide-containing resin is then followed by the same series of events which are continued until the desired peptide has been produced. The finished peptide is then cleaved off the resin under conditions which simultaneously remove all of the individual amino acid side-chain protecting groups.

All reagents used in the synthesis described herein were obtained from standard commercial sources.

Solid phase peptide synthesis was carried out by manual methods using bubbling nitrogen gas as the agitation source for mixing. $N^\alpha$-tert-butyloxycarbonyl (N-t-BOC) protection was used as the temporary protecting group in all the peptide couplings. More specifically, the following resin and protected amino acids were used in a sequential manner: N-t-BOC-L-Arg(Tos)-PAM resin, N-t-BOC-L-Leu, N-t-BOC-D-Phe, N-t-BOC-L-Cys(4-Meb), N-t-BOC-L-Phe, N-t-BOC-Gly, N-t-BOC-L-Hyp(Bzl), N-t-BOC-L-Pro, N-t-BOC-L-Arg(Tos), N-t-BOC-D-Arg(Tos).

Finished peptidyl-resin was dried in vacuo and then placed in the reactor of a Peninsula Laboratories Type I HF apparatus. CP-0126 was cleaved from the resin using standard HF procedures without any carbocation scavengers. After HF removal in vacuo, the resin was washed with diethyl ether and the peptide was extracted from the resin with deionized water.

Two equivalents of the resulting peptide (CP-0126) was allowed to react with 1 equivalent (0.5 molar ratio) of bismaleimidohexane (Pierce) in 0.05M ammonium bicarbonate buffer (pH 8.4) and stirred for 1 hour. The reaction mixture was then concentrated in vacuo and the resulting concentrate redissolved in 0.1M ammonium bicarbonate (pH 5). The solution was loaded in toto onto a column of sulfopropyl (SP) Sephadex (Sigma) and the column eluted with a pH 5–9 gradient over one hour period. The fractions containing the peptide dimer were then combined, concentrated in vacuo, redissolved in deionized water and lyophilized.

The final peptide dimer CP-0127 is assessed for purity by reverse-phase HPLC, amino acid analysis, peptide sequence analysis, and Electro-Spray mass spectrometry.

EXAMPLE 2

Compound CP-0127 may also be prepared in the following manner wherein several separate peptide fragments are prepared, the linking group (BSH) is added to join two fragments and the resulting fragment dimer is then completed by adding the other required peptide fragments.

More specifically, the process involves preparation of the following separate peptide fragments:

(1) Phe-Cys-DPhe (2) Leu-Arg (3) DArg-Arg-Pro (4) Hyp-Gly where appropriate protecting groups are discussed below. Fragments (1) and (2) are joined together to form:

(5) $NH_2$-Phe-Cys-DPhe-Leu-Arg-OFm where OFm is α-fluorenemethyl and Cys is protected with the Acm group. Two molecules of the intermediate (5) may then be joined together through their respective Cys sulfhydryl groups using BMH to give:

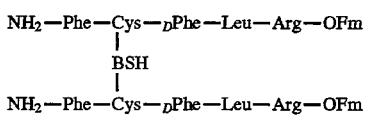

(6)

Fragments (3) and (4) are joined together to form (7) (BOC)-DArg-Arg-Pro-Hyp-Gly-OH where BOC is tert-butyloxycarbonyl, and thereafter two molecules of (7) are joined to (6) to provide:

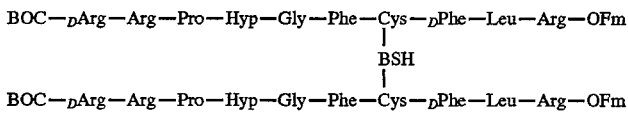

This is followed by removal of the N- and C-terminal protecting groups to give the dimer CP-0127.

This procedure is more specifically outlined hereinafter: Fragment (2) is prepared as follows:

N-T-BOC-Leu (16.68 g, 67 mole) and Arg-OFm.2 HCl (29.68 g, 70 mmole) are dissolved in 140 mL of N,N-dimethylformamide and then 16 mL of diphenylphosphoryl azide (20.43 g, 74 mmole) and 25 mL of diisopropylethylamine (18.55 g, 143 mmole) are added. The reaction proceeds at room temperature until complete by thin layer chromatography (n-butanol:acetic:water 4:1:1) on silica gel.

When complete, the reaction mixture is concentrated in vacuo until about 10% of the original volume is left. The resulting slurry is dissolved in ethyl acetate (150 mL) and washed in a 250 mL separatory funnel with 10% sodium bicarbonate (3×100 mL), water (2×100 mL), 0.1M hydrochloric acid (3×100 mL) and water (2×100 mL). The final organic layer is then dried over sodium sulfate and concentrated to dryness in vacuo.

At this point, the solid or oil is dissolved in a small amount of ethyl acetate and crystallized using hexane. The solid is filtered by vacuum filtration and dried in vacuo.

The N-t-BOC group is removed using 4N HCl in dioxane (100 mL) for 1 hour at room temperature. The solvent is then removed in vacuo and the resulting solid (or oil) dissolved in a small amount of methanol (20 mL). Crystallization is induced by the addition of ethyl ether and the resulting solid is isolated by vacuum filtration, washed with ethyl ether (2×50 mL) and dried in vacuo.

Fragment 4 is prepared using the same procedure. Fragments 1 and 3 are done in an analogous fashion except that an additional amino acid is added. At this point, the N-t-BOC group is left on fragments 1 and 3 and the ester groups are removed as described below.

The esters (methyl or ethyl) are removed by dissolving the peptide in 100 mL methanol and adding 1.5 equivalents of sodium hydroxide; the reaction mixture then being allowed to stir for 1 hour at 0° C. The reaction mixture is neutralized with 1N HCl and concentrated in vacuo to a volume of ca. 30 mL. Water (100 mL) is added and then 1N HCl until the solution pH reaches ca. 1. The peptide is extracted from the aqueous solution with ethyl acetate (2×100 mL) and the combined ethyl acetate is dried over sodium sulfate, filtered and concentrated in vacuo. The resulting oil is dissolved in a small volume of ethyl acetate and crystallized using hexane.

Fragments (1) and (2) are coupled together and worked up in the same manner as described above to give the N-terminal pentapeptide. Fragments (3) and (4) are coupled together and worked up in the same manner as described above to give the C-terminal pentapeptide.

The C-terminal pentapeptide (10 g) is deprotected using 100 mL of 4N HCl in dioxane for 1 hour. The dioxane is removed in vacuo to yield an oil which is dissolved in 20 mL of methanol and treated with excess ethyl ether to produce a white powder. The powder thus produced is dissolved in 90 mL of water and then 10 mL of methanol is added followed by 30 mL of acetic acid saturated with iodine ($I_2$). Stirring is then continued for 1 hour. The reaction mixture is extracted with two equal volumes of chloroform and the water layer lyophilized. The resulting off-white powder is dissolved in 20 mL of water and treated with activated Reductacryl resin (CALBIOCHEM) for 20 minutes. The Reductacryl is removed by filtration and the resin then washed with 20 mL of 0.1M ammonium bicarbonate buffer (pH 8). The combined filtrates containing the peptide are treated with 1.6 g of bismaleimidohexane (Pierce) in 3 mL of N,N-dimethylformamide and stirred for 2 hours. The reaction mixture is then concentrated in vacuo and the resulting concentrate redissolved in 50 mL of 0.1M ammonium bicarbonate buffer (pH 5). The solution is loaded in toto onto a 50 g column of sulfopropyl (SP) Sephadex (Sigma) and the column eluted with a pH 5–9 gradient over a one hour period at 3 mL per minute. The fractions containing the peptide are combined, concentrated in vacuo, redissolved in 100 mL of water and lyophilized.

At this point, 2 equivalents of the N-terminal peptide (fragment 7) is coupled to 1 equivalent of the C-terminal dimer peptide (fragment 6) using the same protocol as described above for fragment 2.

Deprotection of the final peptide is achieved by dissolving 5 g of the peptide in 75 mL of N,N-dimethylformamide containing 30% piperidine and then stirring for 20 minutes. The solvents are removed in vacuo and the resulting oil dissolved in 100 mL of water. The pH is then lowered to ca. 1 with 1N HCl and the product extracted into ethyl acetate (3×100 mL). The combined ethyl acetate is removed in vacuo to yield an oil which is then dissolved in 4N HCl in dioxane and stirred for 1 hour. The dioxane is removed in vacuo and the resulting oil dissolved in 30 mL of methanol. Excess ethyl ether is finally added to yield the product as a white powder.

Final purification of the peptide dimer is carried out by dissolving 5 g in 0.1N ammonium bicarbonate buffer (pH 5), loading the solution onto a 50 g column of sulfopropyl (SP) Sephadex (Sigma) and running a gradient from pH 5 to 9 over a 1 hour period while collecting 10 mL fractions. Each fraction is assessed by analytical HPLC and pure fractions are combined and lyophilized 3 times with water.

The final product is assessed for purity by reverse-phase HPLC, amino acid analysis, peptide sequence analysis, and Electro-Spray mass spectrometry.

In carrying out the above-described synthesis, it is to be noted that the amino group of each amino acid is protected with N-tert-Butoxycarbonyl (N-t-BOC) or the like as needed. The carboxyl group of the amino acids is also protected, in this case with an ester function (e.g., ethyl, methyl or 9-fluorenemetehyl ester). The guanidino side chain of arginine (Arg) is protected as the hydrochloride (HCl) salt and the sulfur atom of cysteine (Cys) is protected using the acetamidomethyl group (Acm).

EXAMPLE 3

Compound CP-0127, prepared as described in Example 1, was compared against the $Cys^6$-modified peptide CP-0126 and the parent peptide CP-0088 for biological activity using tests which are well-recognized in the art. Thus, in vitro studies were performed on standard assay systems, namely, guinea-pig ileum (GPI), rat uterus (RU) and rabbit jugular vein (RJV). It is well known that each of these tissues possesses a BK receptor which is of the $BK_2$ class but each is of a different subtype. The potency of each compound was assessed as a $pA_2$ value according to the method of Arunlakshana & Schild, Br. J. Pharmacol. Chemother., 14:48–58 (1959). The $pA_2$ can be defined as the negative logarithm of the molar concentration of the antagonist in the presence of which the potency of the agonist is reduced two-fold, i.e., twice the amount of agonist is required to produce a given response in the presence of, than in the absence of, the antagonist. A high potency of antagonism is indicated by a high $pA_2$ value. i.e., a low concentration of antagonist is effective.

The percentage recovery (% Rec) was also determined for compounds with respect to each assay. Percentage recovery is a measure of the duration of action, the lower the percentage recovery value, the greater the duration of action of the compound.

The $pA_2$ and percent recovery (% Rec) values obtained for CP-0088, CP-0126 and CP-0127 on the GPI, RU and RJV assays are shown in Table A:

TABLE A

| COM- | GPI | | RU | | RJV | |
|---|---|---|---|---|---|---|
| POUND | $pA_2$ | % REC | $pA_2$ | % REC | $pA_2$ | % REC |
| CP-0088 | 6.6 | 100 | 7.4 | 100 | 8.5 | 90 |
| CP-0126 | 6.4 | 100 | 7.1 | 100 | 8.8 | 60 |
| CP-0127 | 7.7 | 100 | 8.8 | 50 | 10.5 | 10 |

It can be seen that in each tissue, the parent peptide CP-0088 is approximately equipotent with the $Cys^6$-modified peptide (CP-0126). In contrast, the dimer, CP-0127, is significantly more potent than either CP-0126 or CP-0088. The increases in potency for CP-0127 are significantly higher than CP-0126 and CP-0088 in each tissue with the greatest increase being shown on the RJV assay. The increases in potency for CP-0127 vs. CP-0126 on the GPI and RU were less marked but still substantial.

It will also be noted that CP-0127 showed a significantly lower % Rec on the RU and RJV assays than CP-0088 and CP-0126. The % Rec for CP-0127 on the RJV assay was also markedly better than that obtained with CP-0088.

Figure 1B:
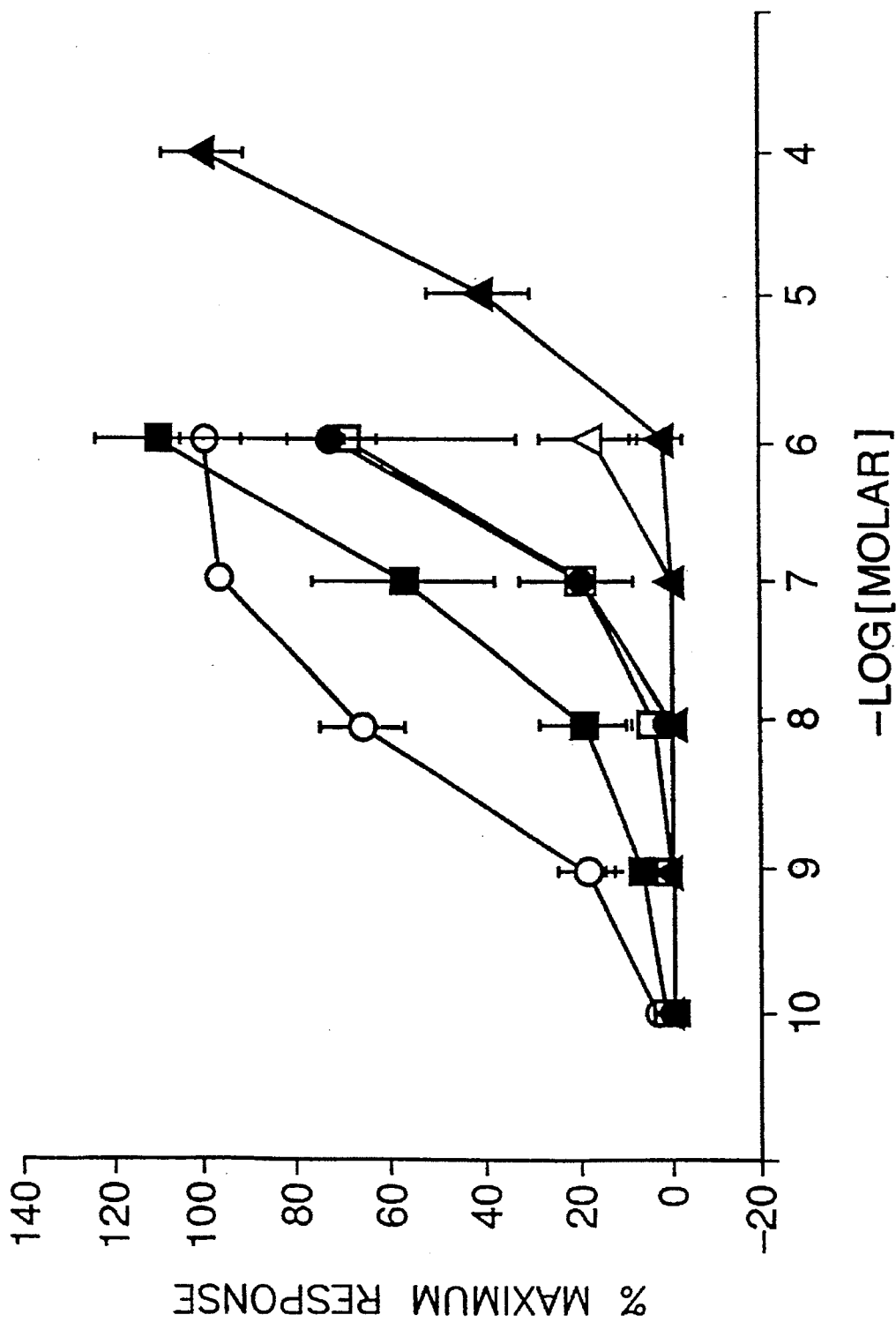
FIG. 1B. Concentration-effect curves to BK in the absence and presence of CP-0127 on rat uterus in vitro. Vertical bars represent standard errors of the means of n=3–4. Note the lack of recovery of the BK curve following an 80 minute washing-off period of the antagonist. (Open circles are BK CONT, N=4; filled circles are BK CP0127–7M, n=3; open triangles are BK CP0127=6M; filled triangles are BK CP0127–5M; open squares are BKREC 1; and filled squares are BKREC 2; $pA_2$=8.8.)

With respect to duration of activity, it is noted that after exposure to the highest concentration of antagonist, each tissue was washed extensively and then assessed for recovery from the antagonist effect. FIGS. 1A and 1B represent the concentration effect curves to BK on rat uterus in vitro using (1A) CP-0126 and (1B) CP-0127. The differences in the BK recovery curves should be noted. As can be seen from FIG. 1A, the concentration effect curve to BK after exposure to CP-0126 almost returns to that seen in the control. In contrast, with CP-0127, there was still significant antagonism of BK even after repeated washings (FIG. 1B). This is an indication that CP-0127 has a longer duration of activity than CP-0126.

EXAMPLE 4

Three in vivo models were used for studies to compare the effects of CP-0126 and CP-0127, These were (a) rabbit skin vascular permeability; (b) BK-induced hypotension in the rat; and (c) LPS-induced hypotension in the anesthetized rat (CP-0127 only) as follows:

(a) Rabbit Skin Vascular Permeability

Figure 2A:
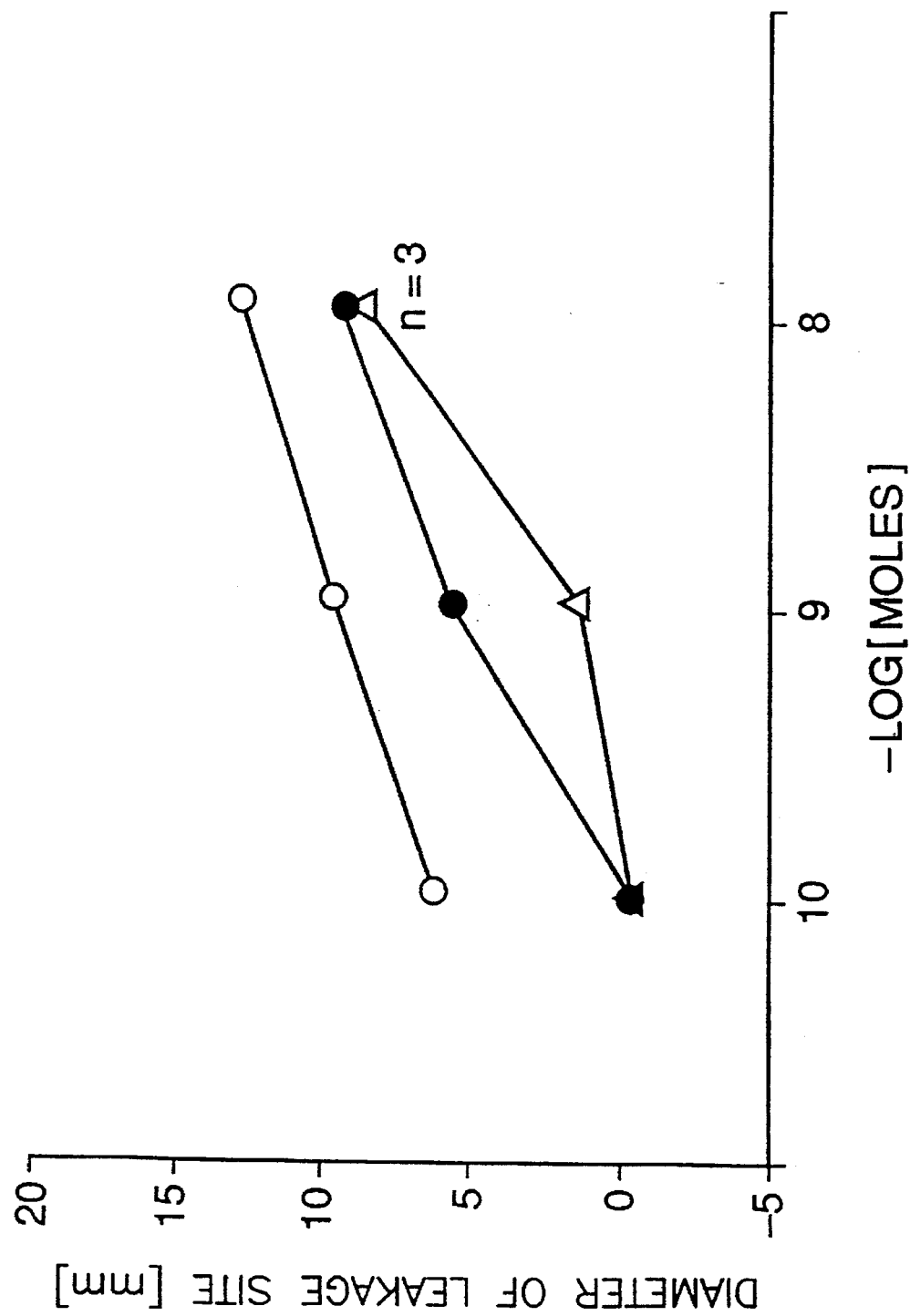
FIG. 2A. Dose curves to BK in the absence and presence of CP-0126 and CP-0127 in the rabbit skin vascular permeability assay. The BK was co-injected with the antagonist, n=3. (Open circles are BK; filled circles are BK+CP0127–8 Moles; open triangles are BK+CP0126–8 Moles.)
Figure 2B:
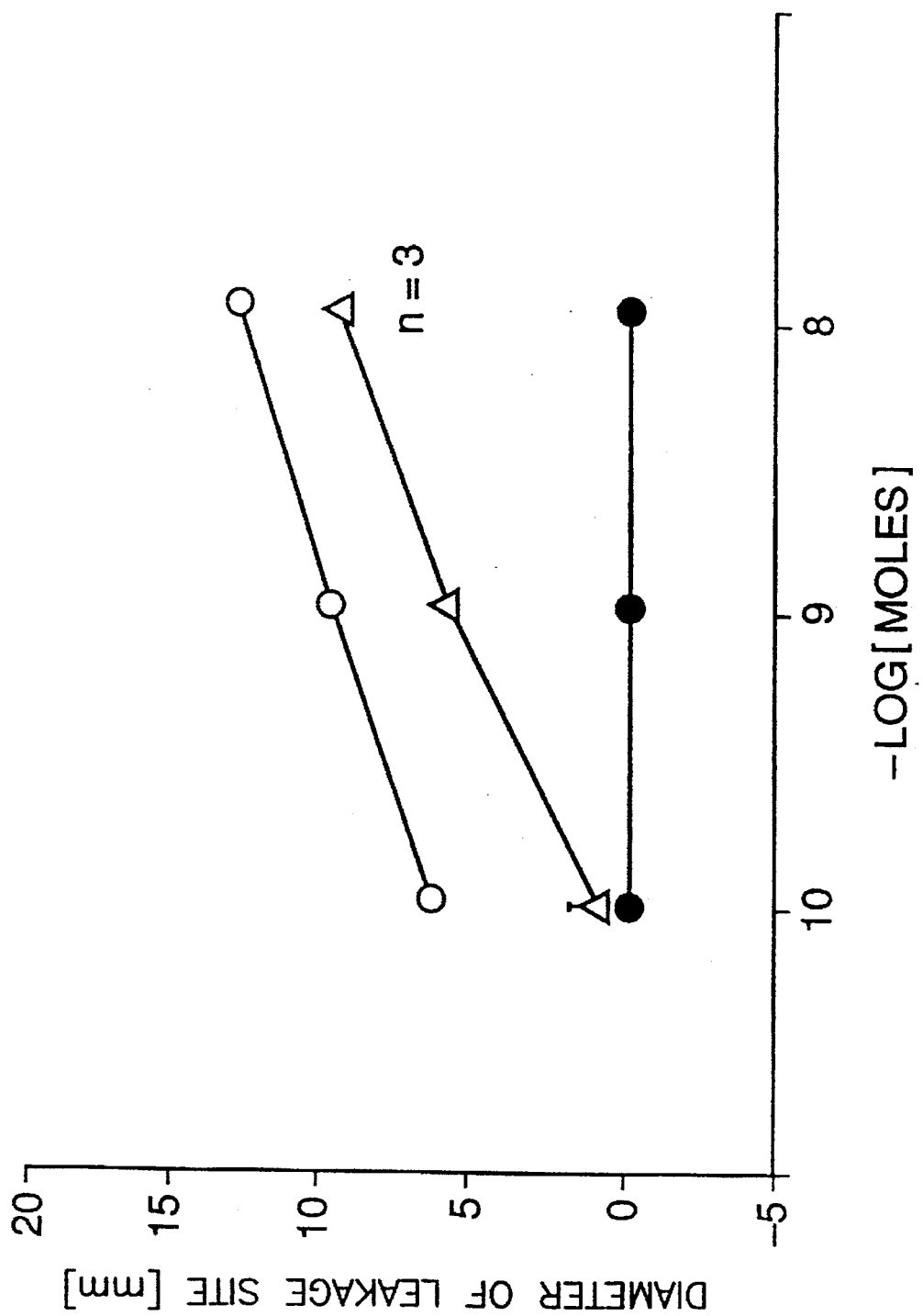
FIG. 2B. Pre-injection of CP0126/7 15 minutes before BK. Dose-response curves to BK in the absence and presence of CP-0126 and CP-0127 in the rabbit skin vascular permeability assay. CP-0126 and CP-0127 were injected 15 minutes before injection of BK into the same site. Vertical bars represent standard errors of the means of n=3. (Open circles are BK; filled circles are BK+CP0127–8 Moles; open triangles are BK+CP0126–8 Moles.)
Figure 2C:
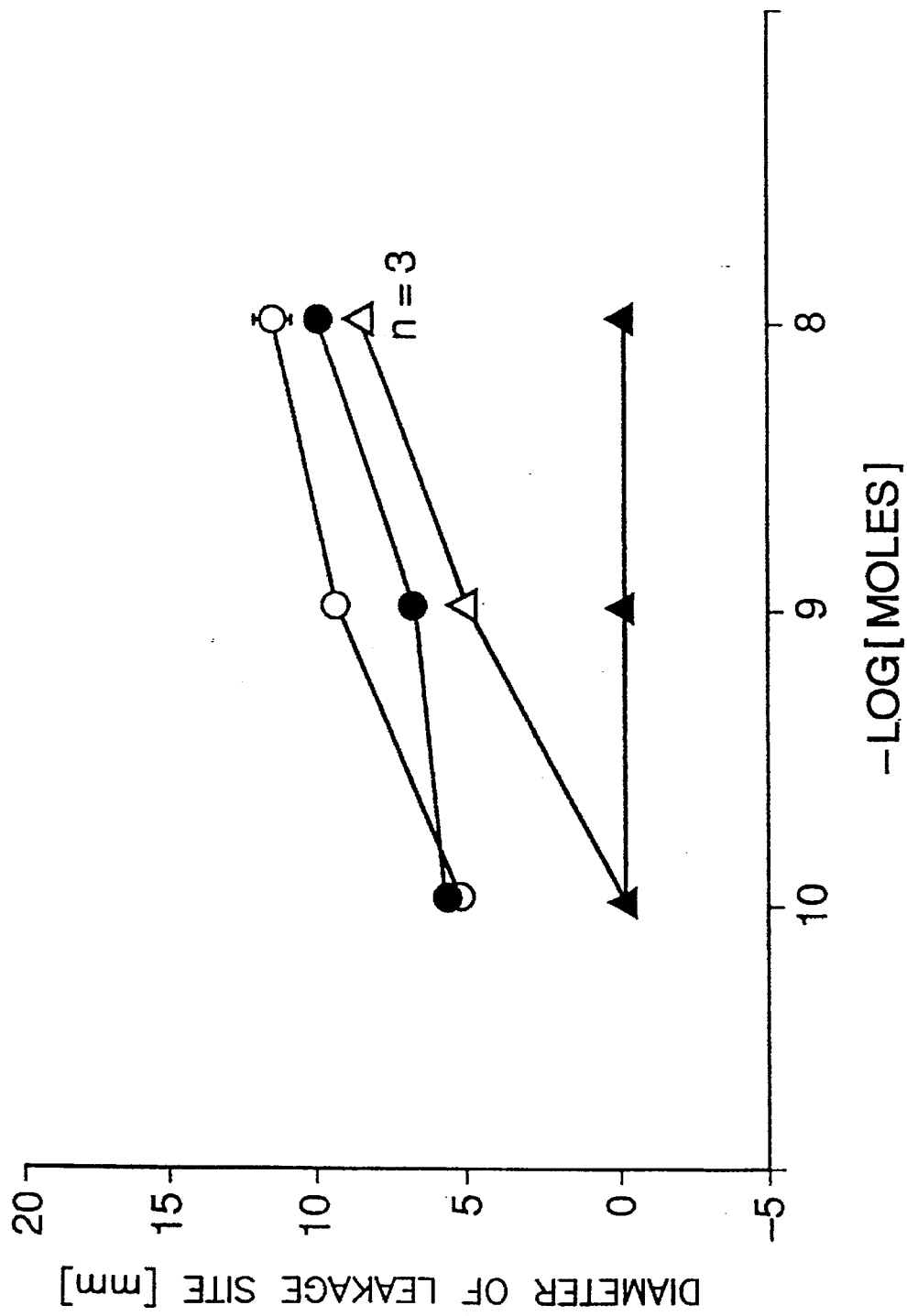
FIG. 2C. Dose-response curves to BK in the absence and presence of saline, CP-0126 and CP-0127 in the rabbit skin vascular permeability assay. CP-0126 and CP-0127 and saline were injected 30 minutes before injection of BK into the same site. Vertical bars represent standard errors of the means of n=3. (Open circles are BK; filled circles are BK+saline; open triangles are BK+CP0126–8 Moles; filled traingles are BK+CP0127–8 Moles.)

In these experiments, two protocols were used. The first protocol used the classical assay in which BK was injected intradermally either alone or in combination with the compound under investigation following intravenous administration of Evans Blue dye. Thirty minutes after intradermal injection of BK with and without the compound, the animal was killed, its skin removed and the area of "blueing" (i.e., vascular permeability or edema) measured. The results using this protocol are shown in FIG. 2A. It can be seen that CP-0126 is more potent than CP-0127 using this protocol. The second protocol involved pre-injecting the test compound either 15 or 30 minutes before injecting BK in the same site. The results are shown in FIGS. 2B and 2C, respectively. It is clear that CP-0127 has totally inhibited responses to bradykinin, whereas CP-0126 is significantly less effective.

(b) Rat Blood Pressure

Figure 3:
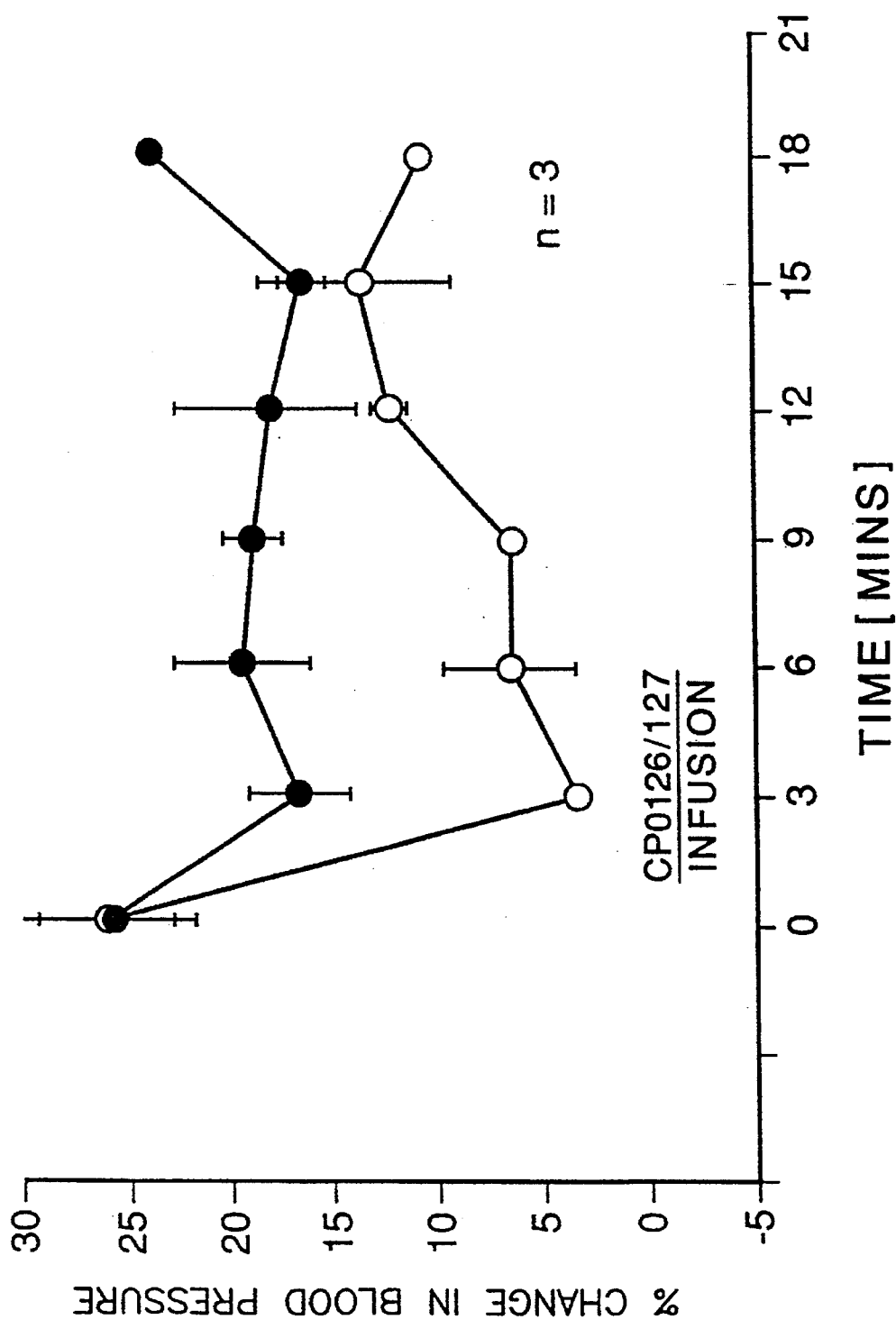
FIG. 3. Effect of CP0126 on blood pressure responses to BK [$4 \times 10^{-9}$ moles] in the rat. Effect of CP-0126 (both 9 nmoles/kg/min i.v.) infused for 5 minutes on the percentage change in blood pressure in the anesthetized rat to single bolus doses of BK ($0.4 \times 10^{-9}$ moles) given at 3 minute intervals, Vertical bars represent standard errors of the means of n=3. (Open circles are CP0127 9 nmoles/kg/min.i.v.; filled circles are CP0126 9 nmoles/kg/min.i.v.)

A comparison of the antagonist potency of CP-0126 and CP-0127 was made in anesthetized rats. Following calculation of the hypotension dose-response curve to BK in these animals, the minimum dose producing maximal reduction in blood pressure was repeated at approximately three minute intervals before, during and after an intravenous infusion of either CP-0126 or CP-0127 at 9 nmol $kg^{-1}$ $min^{-1}$. FIG. 3 shows the results obtained in terms of the percentage change in mean arterial blood pressure in the rat to BK ($4 \times 10^{31\ 9}$ moles) before, during and after an intravenous infusion of either CP-0126 or CP-0127 at 9 nmol $kg^{-1}$ $min^{-1}$. It can be seen from FIG. 3 that CP-0127 almost totally inhibited responses to this large dose of BK whereas CP-0126 was almost totally ineffective. After stopping the infusion of CP-0127, it can be seen that the responses to BK returned slowly being fully recovered after approximately 20 minutes.

(c) Lipopolysaccharide (LPS) Induced Hypotension in the Anesthetized Rat

Figure 4:
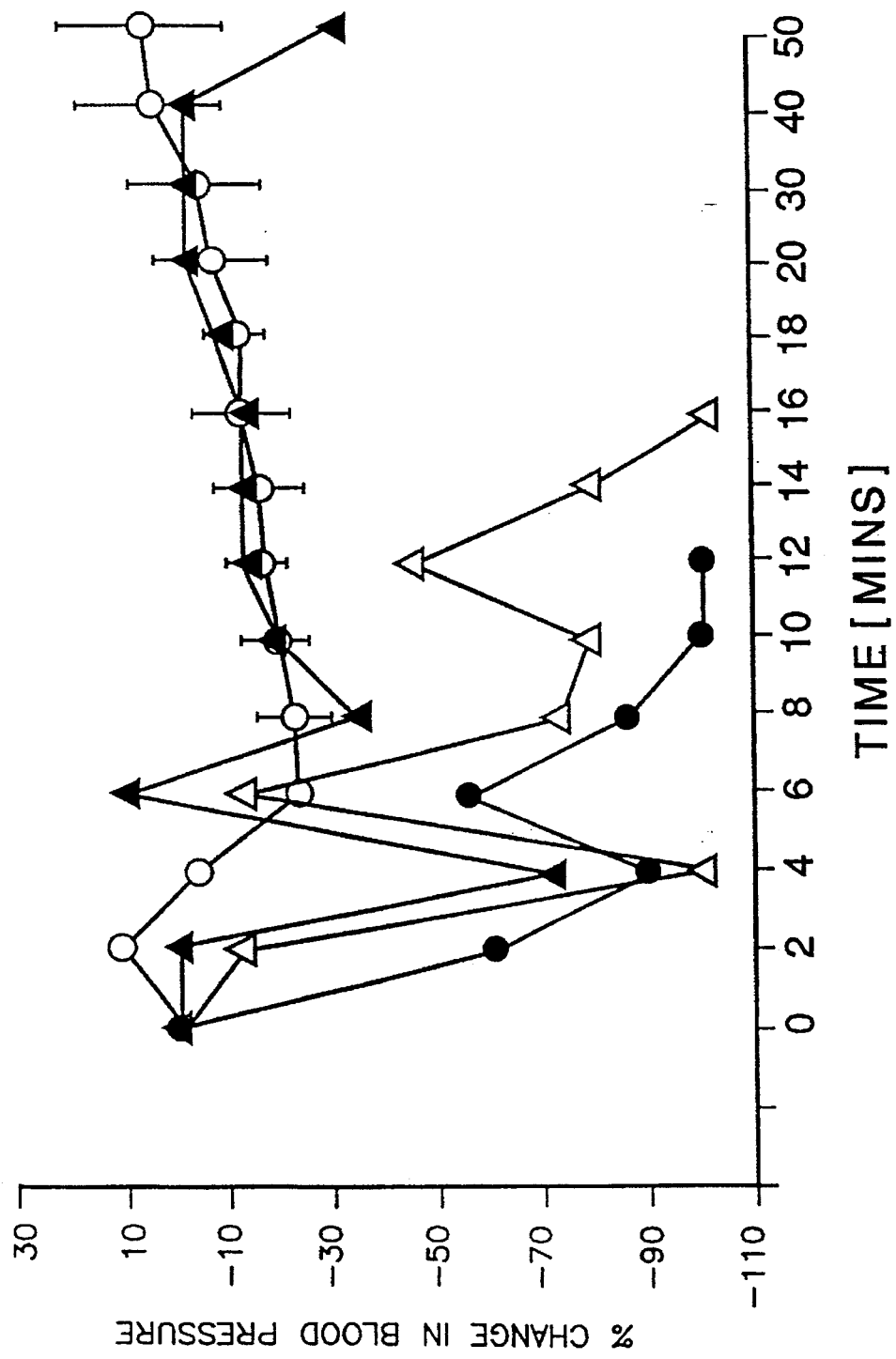
FIG. 4. Effect of CP0127, 18 nmole/kg/min. i.v., 60–90 min before, during and after an i.v. injection of LPS 15 mg/kg. Blood pressure response of anaesthetized rats infused with saline or CP-0127 18 nmoles kg/min i.v. 60–90 minutes before, during and after an i.v. bolus of L.P.S. from *E. Coli*, 15 mg/kg. Vertical bars represent standard errors of the means of n=3 for the CP-0127 group. The saline treated rats are plotted individually for comparison. (Open circles are CP0127 n=3; filled circles are saline Rat 1 who died; open triangles are saline Rat 2 who died; filled triangles are saline Rat 3; filled triangle drop off represents severe resp. distress.)
Figure 5B:
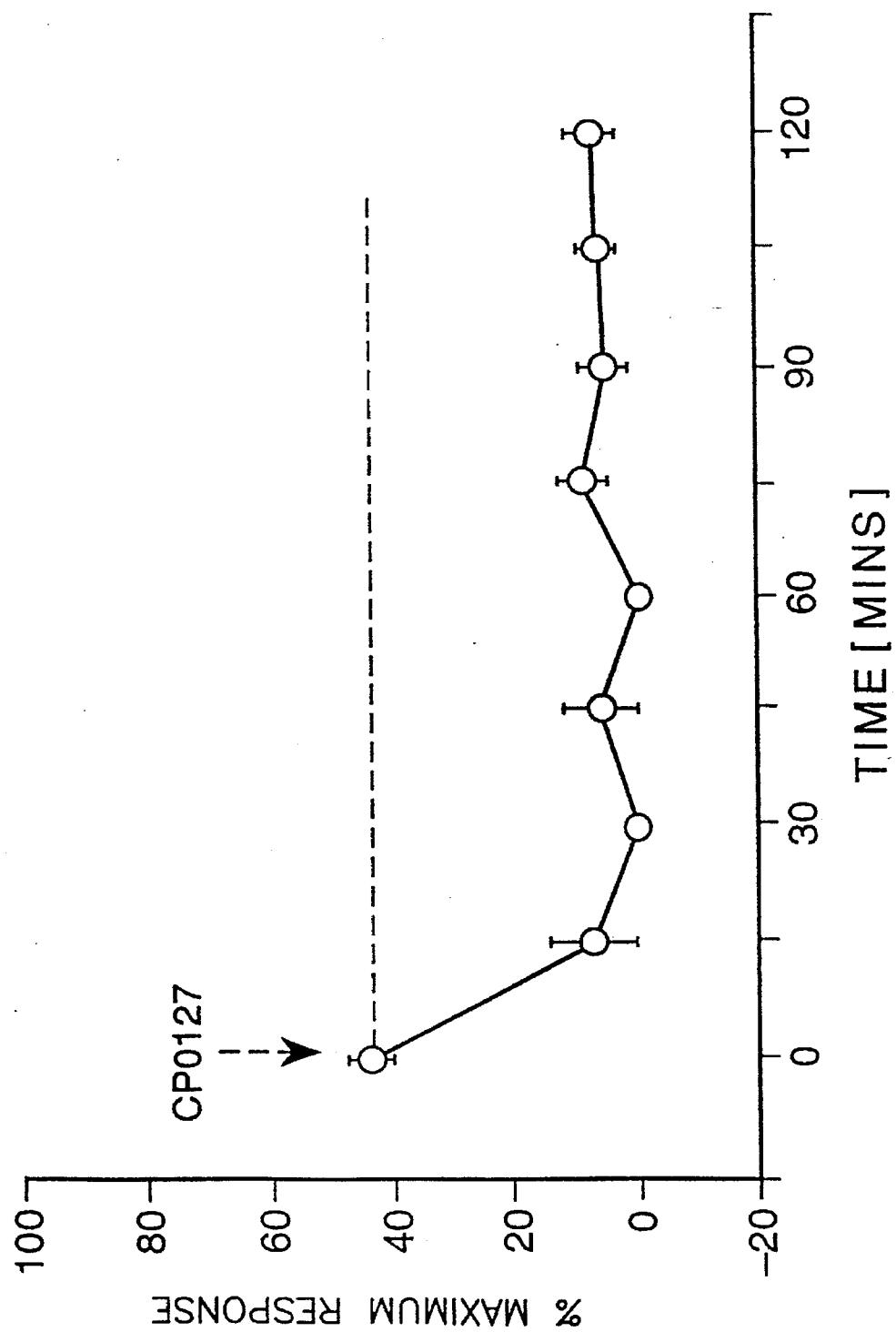
FIG. 5B. Rat blood pressure response to BK (0.4 nmoles) before and after CP0127 3.6 um/kg s.c. Blood pressure responses to the $ED_{50}$ (0.4 nmoles) of BK (derived from FIG. 5A) before and at 15 minute intervals after a single s.c. injection of CP-0127, 3.6 nmole/kg. Responses are expressed as the percentage of the original BK maximum response. Vertical bars represent standard errors of the means of n=3.

LPS-induced hypotension in the rat is a standard animal model of septic shock. In this model, anesthetized rats are injected intravenously with LPS from Eschericha coli at 15 mg $kg^{-1}$. This produces an immediate and profound drop (50–60% change) in mean arterial blood pressure (FIG. 4). When CP-0127 was infused at 18 nmol/$kg^{-1}$/$min^{-1}$ intravenously 60 minutes before, during and after the injection of LPS there was a significant attenuation of the immediate drop in blood pressure which then rapidly recovered back to normal. Normotension was then sustained for the duration of the experiment (approximately 3–4 hours). This was in contrast to the control group in which profound hypotension was sustained. In fact, 3 animals died within 20 minutes of LPS injection. See FIG. 4 which illustrates the percentage change in mean arterial blood pressure in the anaesthetized rat to an intravenous bolus injection of LPS, 15 mg $kg^{-1}$.

The data referred to above shows that the dimer BK antagonist (CP-0127) is significantly more potent than the $Cys^6$ monomer antagonist (CP-0126) in both in vitro and in vivo models of BK activity using standard assay systems to evaluate the efficacy of the antagonists against a specific stimulus (i.e., BK) and against a non-specific stimulus (LPS) in a recognized animal model of septic shock.

The in vitro data demonstrate exceptional potency of CP-0127 on each assay tissue, the most marked activity being seen on the rabbit jugular vein. As noted, compound CP-0088 was chosen from the literature for test purposes because it was the most potent (assessed by standard $pA_2$ determination) BKA in classical in vitro assay systems reported. Using the same criteria ($pA_2$ determination), the potency of CP-0127 appears to surpass most if not all of the previous BKAs that have been reported, particularly on rabbit jugular vein.

The highest $pA_2$ value for CP-0127 was obtained on a vascular preparation, the rabbit jugular vein and it appears that this class of BKA should be suitable for treating vascular processes where BK is involved. Thus, when viewed in the light of BK's role in inflammation, the effects of CP-0127 on permeability/edema and vasodilation are of particular relevance. The data from the skin vascular permeability studies are of interest since CP-0126 was found to be more effective than CP-0127 when both antagonists were co-injected with BK. However, when CP-0127 and CP-0126 were pre-injected either 15 to 30 minutes before challenging with BK, CP-0127 totally inhibited responses to BK whereas CP-0126 was much less effective than when co-injected with BK. The reason for this difference is not understood but it may be that the dimer requires more time for equilibration with the receptor and once bound is more difficult to displace compared with the monomer. In addition, it appears that CP-0127 may be more metabolically stable than CP-0126.

As noted earlier, there is strong evidence that BK is significantly involved in septic shock due to gram negative bacterial infection. In this connection, it is to be noted that the present dimer (CP-0127) totally reversed the response to LPS at a dose that effectively blocked hypotensive responses to maximal doses of BK in the anesthetized rat. Although CP-0126 has not been assessed in the LPS septic shock model, it is believed that, at the same dose, it would be much less effective than CP-0127 considering the lack of effect of this compound (CP-0126) against high doses of BK.

Thus, in brief, from the in vitro and in vivo data provided herein, there are significant quantitative differences between the monomeric (CP-0126) and dimeric (CP-0127) BK antagonists with respect to absolute potency, resistance to wash-off and duration of action.

In considering the bioavailability of CP-0127, it has been demonstrated, using a single dose (3.6 µmol $kg^{-1}$) given subcutaneously (S.C.) that the blood pressure and pain responses to BK can be totally blocked for at least 2 hours (the duration of the experiments). Using anaesthetized rats, dose-response curves to BK were constructed and the $ED_{50}$ identified (see FIG. 5a). The $ED_{50}$ was then injected before and at 15 minute intervals after a single S.C. injection of CP-0127, From FIG. 5b, it can be seen that the response to BK is totally blocked for the duration of the experiment (2 hours).

In a separate set of experiments, pain in response to the intra-arterial injection of BK was assessed in conscious rats which had previously (48 hours before) been implanted with an indwelling cannula into the carotid artery. Bradykinin (20 nmoles $kg^{-1}$) was injected intra-arterially which produced a characteristic contralateral paw elevation, and head and body rotation, followed by a period of quiescence. The response was quantified as a ranking scale of 0–5 reflecting the degree of behavioral response observed.

Figure 6:
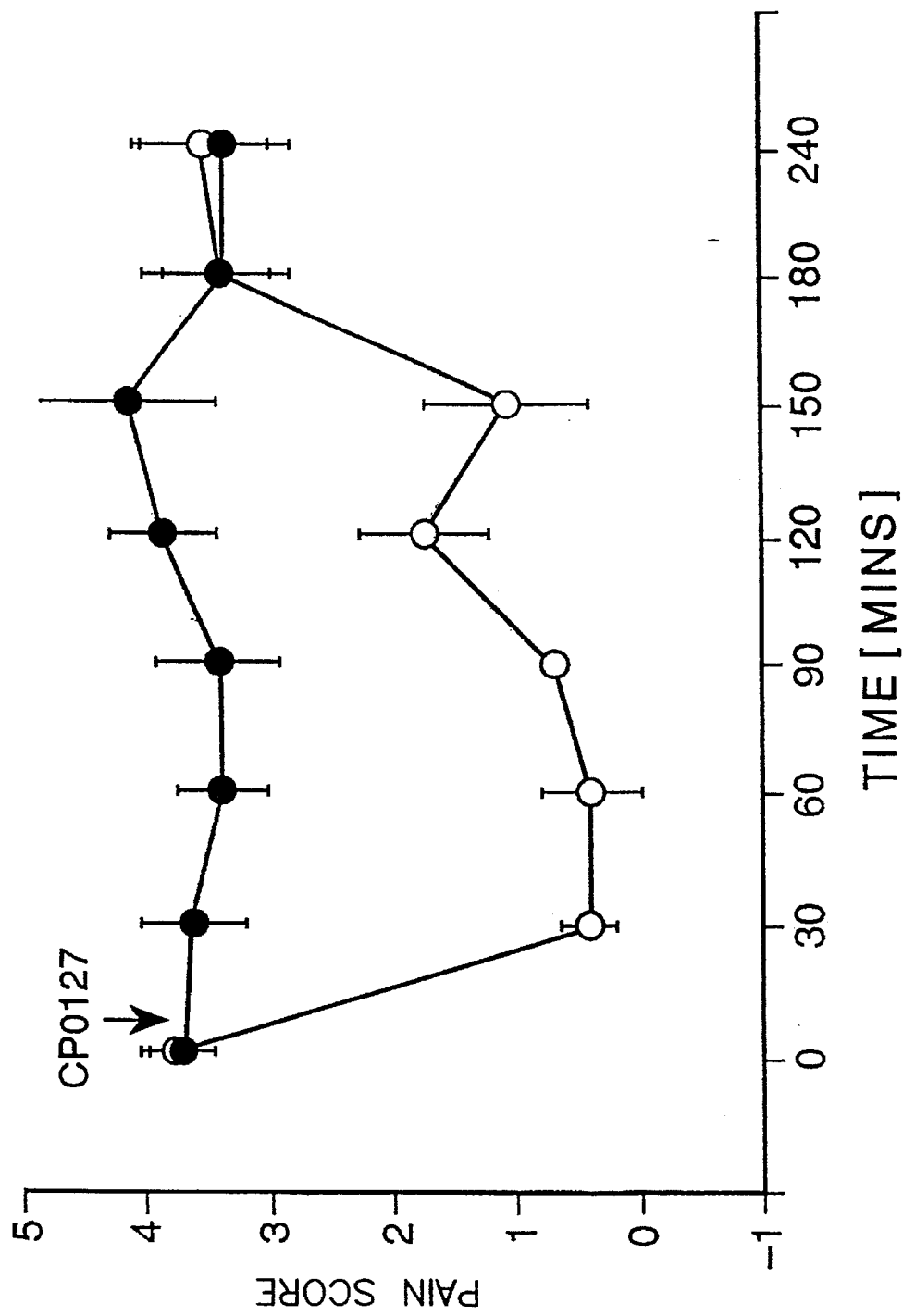
FIG. 6. Effect of CP0 127 3.6 umol/kg s.c. on the pain response to an intra-arterial injection of bradykinin 20 nmoles/kg in the rat. Pain response to a single intraarterial injection of BD (20 nmoles/kg) in conscious rats injected with saline or CP-0127, 3.6 umole/kg s.c. Vertical bars represent standard errors of the means of n=3–9. (Filled circles are saline, n=9; open circles are CP0127, n=3–9.)

The data shown in FIG. 6 demonstrate that a single S.C. injection of CP-0127 at 3.6 µmol $kg^{-1}$ totally abolished the response to BK with inhibition lasting for the duration of the experiment (approximately 2 hours). Controls showed a stable response pattern during the entire experimental period.

EXAMPLE 5

This example illustrates the effect of introducing the Cys residue and consequently the linker into different positions along the chain of CP-0088, The various compounds identified in Table B below were prepared following the procedure of Example 1 with the Cys moiety introduced into the parent CP-0088 at the position indicated followed by reaction between the sulfhydryl group of the Cys residue and BMH to provide dimers as indicated. The Cys-modified monomers and the resultant dimers were tested for activity on guinea pig ileum in vitro on the standard tissue bath/strain gauge system as before. The results obtained in terms of $pA_2$, together with those for CP-0088, CP-0126 and CP-0127, are given in Table B. The references to "L" and "D" are used to show that optical isomers were involved as indicated.

TABLE B

| COMPOUND NUMBER | COMPOSITION | DESCRIPTION REFERENCE | $pA_2$ GUINEA PIG ILEUM |
|---|---|---|---|
| CP-0088 | 0 1 2 3 4 5 6 7 8 9<br>DR—R—P—J—G—F—S—DF—L—R | Monomer | 6.5 ± 0.2 |
| CP-0126 | L—CYS$^6$ | Monomer | 6.6 ± 0.1 |
| CP-0127 | L—CYS$^6$ | Dimer | 7.7 ± 0.2 |
| CP-0140 | L—CYS$^0$ | Monomer | 6.7 ± 0.1 |
| CP-0152 | L—CYS$^0$ | Dimer | <6 |
| CP-0149 | D—CYS$^0$ | Monomer | 6.7 ± 0.5 |
| CP-0161 | D—CYS$^0$ | Dimer | 6.5 ± 0.1 |
| CP-0141 | L—CYS$^1$ | Monomer | 6.1 ± 0.1 |
| CP-0153 | L—CYS$^1$ | Dimer | 7.6 ± 0.6 |
| CP-0142 | L—CYS$^2$ | Monomer | <6 |
| CP-0154 | L—CYS$^2$ | Dimer | 6.9 ± 0.3 |
| CP-0143 | L—CYS$^3$ | Monomer | 6.7 ± 0.4 |
| CP-0155 | L—CYS$^3$ | Dimer | 7.7 ± 0.2 |
| CP-0136 | L—CYS$^4$ | Monomer | Inactive |
| CP-0137 | L—CYS$^4$ | Dimer | Inactive |
| CP-0173 | D—CYS$^4$ | Monomer | Inactive |
| CP-0203 | D—CYS$^4$ | Dimer | Inactive |
| CP-0144 | L—CYS$^5$ | Monomer | 6.4 ± 0.2 |
| CP-0156 | L—CYS$^5$ | Dimer | 7.9 ± 0.1 |
| CP-0145 | L—CYS$^7$ | Monomer | Inactive |
| CP-0157 | L—CYS$^7$ | Dimer | Inactive |
| CP-0146 | D—CYS$^7$ | Monomer | Inactive |

TABLE B-continued

| COMPOUND NUMBER | COMPOSITION | DESCRIPTION REFERENCE | $pA_2$ GUINEA PIG ILEUM |
|---|---|---|---|
| CP-0158 | D—CYS$^7$ | Dimer | Inactive |
| CP-0147 | L—CYS$^8$ | Monomer | Inactive |
| CP-0159 | L—CYS$^8$ | Dimer | Inactive |
| CP-0148 | L—CYS$^9$ | Monomer | Inactive |
| CP-0160 | L—CYS$^9$ | Dimer | Inactive |

The above results indicate that the rank order of potency of the dimers shown in Table B, listed by linking position, is:

$$5 \geq 6 \geq 1 \geq 2 > 3 > 0 >> 4, 7, 8, 9$$

with the 4, 7, 8 and 9 position dimers inactive. Table B further shows that all active dimers with Cys in the 1, 2, 3, 5 and 6 positions were more potent than the corresponding monomer. This is true for both the L- and D- isomeric forms where determined.

EXAMPLE 6

The $pA_2$ and % recovery values on the rat uterus model of BK activity were determined for the various monomers and dimers referred to in Example 5 and compared with the corresponding values obtained for reference compound CP-0088, CP-0127 and the parent Cyst-containing monomer (CP-0126). The results are shown below in Table C.

aspect of the specific linker chosen, BMH. Listed below (Table D) are a series of dimers that were derived from the base compound CP-0126 and a variety of bismaleimidoalkane linkers. These data clearly indicate that various bismaleimidoalkanes can be used to form effective BK antagonist dimers. The selection of a preferred compound will depend on the intended application based upon the specific pharmacodynamic qualities desired.

TABLE C

| MONOMER | | DIMER | $pA_2$ MONOMOER | $pA_2$ DIMER | % REC MONOMER | % REC DIMER |
|---|---|---|---|---|---|---|
| CP-0088 | — | — | 7.4 ± 0.2 | — | 100 | — |
| CP-0126 | (L—CYS$^6$) | CP-0127 | 7.1 ± 0.1 | 8.8 ± 0.3 | 100 | 50 |
| — | — | — | — | — | — | — |
| CP-0144 | (L—CYS$^5$) | CP-0156 | 7.2 ± 0.1 | 8.1 ± 0.1 | 95 | 75 |
| CP-0136 | (L—CYS$^4$) | CP-0137 | Inactive | Inactive | — | — |
| CP-0173 | (D—CYS$^4$) | CP-0203 | Inactive | Inactive | — | — |
| CP-0143 | (L—CYS$^3$) | CP-0155 | P.A.* | 6.4 ± 0 | — | 100 |
| CP-0142 | (L—CYS$^2$) | CP-0154 | 6.4 ± 0.2 | P.A.* | 80 | 90 |
| CP-0141 | (L—CYS$^1$) | CP-0153 | <6 | 7.7 ± 0.2 | 100 | 100 |
| CP-0140 | (L—CYS$^0$) | CP-0152 | 7.1 ± 0.4 | 7.9 ± 0.1 | 50 | 50 |
| CP-0149 | (D—CYS$^0$) | CP-0161 | 7.1 | 6.5 | 75 | 100 |
| CP-0145 | (L—CYS$^7$) | CP-0157 | Inactive | Inactive | — | — |
| CP-0146 | (D—CYS$^7$) | CP-0158 | Inactive | Inactive | — | — |
| CP-0147 | (L—CYS$^8$) | CP-0159 | Inactive | Inactive | — | — |
| CP-0148 | (L—CYS$^9$) | CP-0160 | Inactive | Inactive | — | — |

*P.A. = partial antagonist

While the relative potencies shown in Table C for the rat uterus model were somewhat different from those obtained in Example 5 on the guinea pig ileum, it is noteworthy that the compounds based on the Cys modification in the 4, 7, 8 and 9 positions of CP-0088 were again inactive. Additionally, the rat uterus results indicate a preference for the "6" position modification although it will be recognized that other positions may well be preferred with other linkages and modifications depending, for example, on the receptor types or subtypes involved.

EXAMPLE 7

While the data generated from the homodimer CP-0127 indicate that this compound is a significant improvement over other compounds in the literature, it is important to realize that the effects of dimerization are not a unique

TABLE D

EFFECT OF LINKER LENGTH

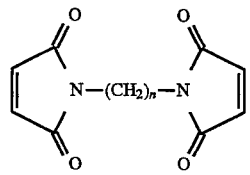

| # of CARBON ATOMS | COMPOUND NO. | $pA_2$ (UTERUS) | % REC (40 MIN) |
|---|---|---|---|
| n = 2 | CP-0162 | 8.4 ± 0.2 | 90 |
| n = 3 | CP-0172 | 8.6 ± 0.2 | 90 |
| n = 4 | CP-0209 | 8.2 ± 0.2 | 50 |
| n = 6 | CP-0127 | 8.8 ± 0.3 | 50 |
| n = 8 | CP-0211 | 8.4 | 25 |

TABLE D-continued

EFFECT OF LINKER LENGTH

| # of CARBON ATOMS | COMPOUND NO. | $pA_2$ (UTERUS) | % REC (40 MIN) |
|---|---|---|---|
| n = 9 | CP-0229 | 9.3 ± 0.4 | 0–10 |
| n = 10 | CP-0230 | 8.6 ± 0.2 | 0 |
| n = 12 | CP-0166 | 8.2 ± 0.3 | 0* |

*IRREVERSIBLE AT 80 MINUTES

EXAMPLE 8

The following compounds according to the invention were also prepared as modifications of CP-0126:

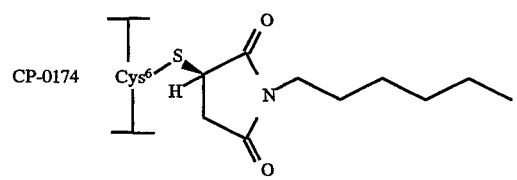

CP-0174

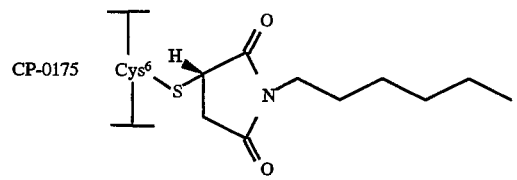

CP-0175

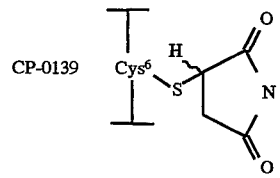

CP-0139

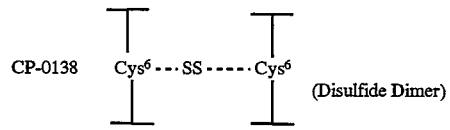

CP-0138 (Disulfide Dimer)

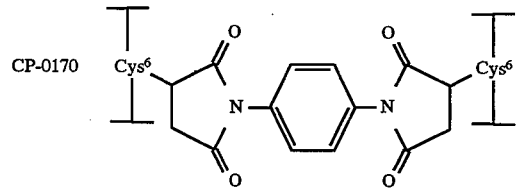

CP-0170

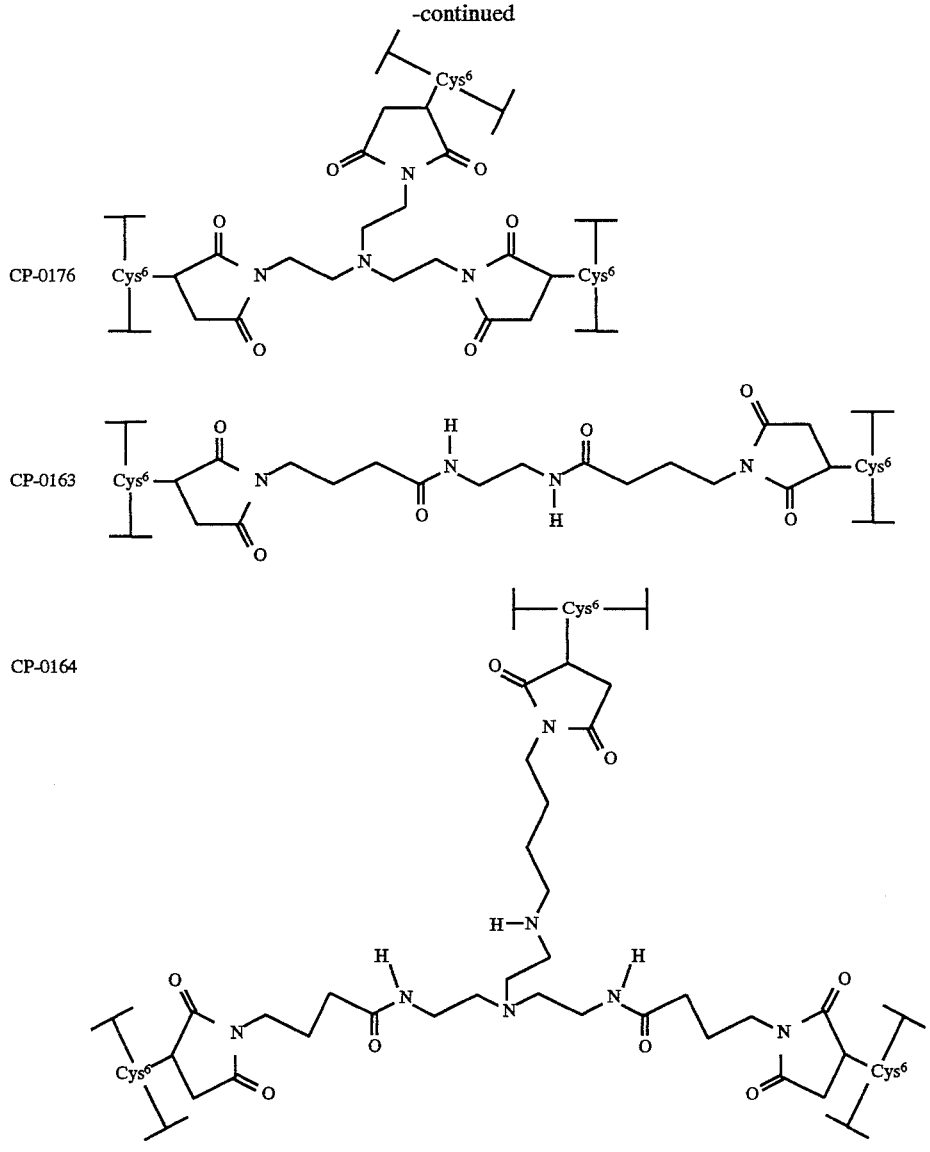

represents CP-0126. These compounds were prepared by reacting CP-0126, i.e.

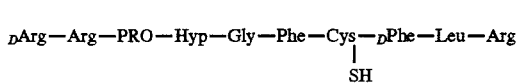

with the indicated linker compound essentially in the manner described in Example 1.

As will be appreciated, the listed compounds include modified peptide monomers (CP-0174, -0175, -0139); dimers (CP-0138, -0163 and -0170) and the trimers (CP-0164 and -0176).

Table E compares the $pA_2$ values obtained on testing the above compounds for activity in the guinea pig ileum (GPI) and rat uterus tests with CP-0126 and CP-0127:

TABLE E

| COMPOUND | GPI $pA_2$ | RAT UTERUS $pA_2$ | % RECOVERED |
|---|---|---|---|
| CP-0126 | 6.6 ± 0.2 | 7.1 ± 0.1 | 100 |
| CP-0127 | 7.7 ± 0.2 | 8.8 ± 0.3 | 50 |
| CP-0174 | 7.2 | 8.4 | 50 |
| CP-0175 | 7.2 | 8.5 | 30 |
| CP-0139 | 6.2 ± 0.2 | 7.3 ± 0.2 | 100 |
| CP-0138 | 7.2 ± 0.1 | 8.0 ± 0.1 | 100 |
| CP-0163 | 8.2 ± 0.2 | 7.6 ± 0.3 | 100 |
| CP-0164 | 7.5 | 7.6 | 50 |
| CP-0170 | 6.3 | 7.1 ± 0.4 | 100 |
| CP-0176 | 7.0 | 8.6 | 50 |

The data given in Tables D and E shows the following:

1. Reacting the cysteine in the "6" position with free maleimide thereby converting it into an S-succinimido-L-cysteine improves potency (compare CP-0126 with CP-0139, -0174, -0175). However, it has also been found that monomers as a class behave differently to dimers as a class with respect to their resistance to "wash-off" regardless of their structure. Monomers can be removed and the dose/response profile of the tissue returns to pre-treatment status with one exchange of buffer while dimers require multiple washings to reverse their activity and return the system to baseline. This aspect of monomer vs. dimer activity in vitro models of BK antagonism is indicative of prolonged duration of action for the dimers in vivo.

2. Improved potency with dimerization does not appear to be dramatically influenced by the linker as long as the linker is linear and flexible. However, a more rigid or constrained linker (CP-0170) does not improve potency with respect to the corresponding monomer (CP-0126). To underscore this point, the disulfide dimer (CP-0138), which is probably the most constrained and rigid of the dimers tested, is also relatively less active. In fact, it is no different in inhibitory activity than the CP-0126 monomer in this system.

3. Trimerization (CP-0164 and CP-0176) does not appear to improve potency beyond that which was obtained by dimerization (CP-0127, -0163 and -0166).

EXAMPLE 9

To show the generalizability of this concept with respect to the ligand, another representative BKA (CP-0181):

$_{D}$Arg$^{0}$-Arg$^{1}$-Pro$^{2}$-Hyp$^{3}$-Gly$^{4}$-Phe$^{5}$-Ser$^{6}$-$_{D}$Phe$^{7}$-Phe$^{8}$-Arg$^{9}$ was modified by introducing Cys in the "6" position and dimerizing with BMH to form a BSH dimer, (CP-0215).

The $pA_2$ values on the rat uterus assay and percent recovery were determined for this BSH dimer and compared with CP-0088 and CP-0127. The results are shown below in Table F and it will be noted that improved $pA_2$ results and percent recovery were realized for both dimers when compared with their corresponding reference monomers:

It will be appreciated from the foregoing that various modifications may be made without departing from the spirit and scope of the invention. For example, while the BK antagonist designated as CP-0088 has been modified by inserting Cys at various positions in the preparation of the illustrated dimers, any parent antagonist may be used to form useful dimers or the like without any modification or with a different type of modification. The linker used to form the compounds of the invention may also be varied, as noted earlier. As a further illustration of this aspect of the invention, it is noted that the linker may comprise dextran which may be modified randomly along the length of the dextran molecule so as to ultimately possess reactive maleimide residues as shown below:

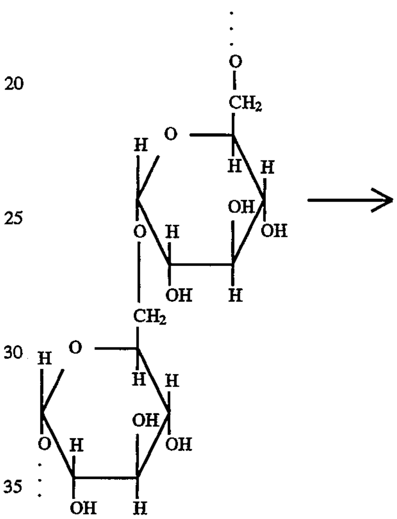

DEXTRAN

TABLE F

| COMPOUND | RAT UTERUS $pA_2$ | % RECOVERY |
|---|---|---|
| CP-0088<br>$_{D}$ARG$^{0}$—ARG$^{1}$—PRO$^{2}$—HYP$^{3}$—GLY$^{4}$—PHE$^{5}$—SER$^{6}$—$_{D}$PHE$^{7}$—LEU—ARG | 7.4 | 100 |
| CP-0127<br>BSH (CYS$^{6}$) Dimer Of CP-0088 | 8.8 | 50 |
| CP-0181<br>$_{D}$ARG$^{0}$—ARG$^{1}$—PRO$^{2}$—HPY$^{3}$—GLY$^{4}$—PHE$^{3}$—SER$^{4}$—$_{D}$PHE$^{7}$—PHE$^{8}$—ARG$^{9}$ | 7.0 | 100 |
| CP-0215<br>BSH (CYS$^{6}$) Dimer Of CP-0181 | 8.2 | 40 |

The foregoing results (Examples 3–9) show that the dimers are more effective than either the parent or modified antagonist and that trimers, while better than the monomers, do not show improvement over dimers. It is also believed that the best results are obtained using reactive bismaleimido moieties which are themselves preferably joined by a simple straight hydrocarbon chain, as the peptide linking group. The introduction of two new chiral centers following peptide addition to give optically different compounds (i.e., diastereomers) does not seem to impact undesirably on the antagonist activity.

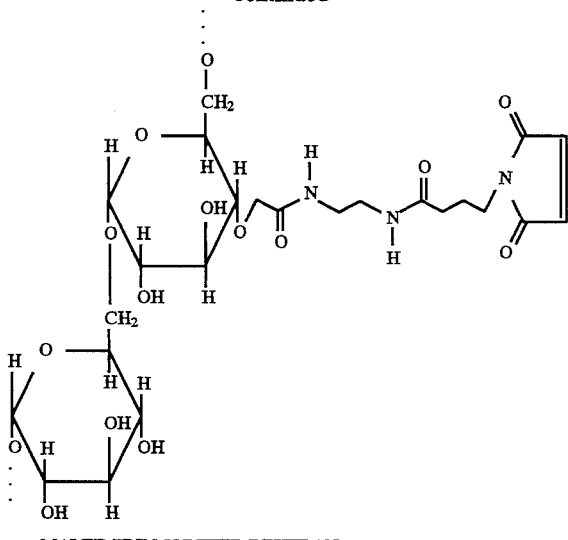

MALEIMIDE MODIFIED DEXTRAN

The resulting maleimide-substituted dextran can then be reacted with a free sulfhydryl containing peptide in a fashion analogous to that previously described at varying molar ratios to yield peptide-dextran conjugates of various substitution densities and overall size.

As noted earlier, an important aspect of the invention is the provision of hetero-dimers or higher hetero- "mers" where different BKAs are used to provide the compounds of Formula (I). This "hetero" embodiment makes it possible to design dimers, for example, which are effective against two or more different bradykinin receptors, e.g. $BK_1$ and $BK_2$ receptors. These two receptors appear to be the most abundant and apparently have the greatest distribution in various tissues. In general, $BK_1$ receptor ligands (both agonists and antagonists) are formed when the C-terminal arginine is removed from the corresponding $BK_2$ receptor ligand by either circulating or tissue associated carboxypeptidases.

Examples of this conversion from $BK_2$ to $BK_1$ selectivity are seen with the conversion of bradykinin to des-$Arg^9$-BK and kallidin to des-$Arg^{10}$-kallidin. This suggest that it would be preferable for a general BK antagonist to contain both $BK_1$ and $BK_2$ receptor antagonist activity. On the other hand, there may be situations where the antagonist should selectively effective against $BK_1$ or $BK_2$ receptors alone.

The distribution and relative importance of these two receptor systems varies from tissue to tissue and species to species. In addition, various pathophysiologic processes can alter the distribution and importance of these two. receptor systems over time within the same animal. In other words, the receptor distribution in the naive animal may be considerably different from the receptor distribution in that same animal after a pathophysiologic process (sepsis for example), has gone on for some time (see, Marceua, F. et al, in "Pharmacology of Kinins: Their Relevance to Tissue Injury and Inflammation", General Pharmacology, 14, pp.209–229). As a result, it is difficult to know what type of antagonist is most appropriate for any given application and relying on the in vivo conversion of a $BK_2$ antagonist to a $BK_1$ antagonist may not be feasible in certain circumstances. The provision of heterodimers according to the invention offers the possibility of dealing with such situations where, for example, both $BK_1$ and $BK_2$ receptors are involved.

Representative heterodimers according to the inventions, based on the indicated $BK_2$ and $BK_1$ antagonist monomers are listed below:

$BK_2$ ANTAGONIST MONOMERS

CP-0126: $_D$ARG—ARG—PRO—HYP—GLY—PHE—CYS—$_D$PHE—LEU—ARG
                                                                    |
                                                                    SH

CP-0185: $_D$ARG—ARG—PRO—HYP—GLY—PHE—CYS—$_D$(Tic)—Oic—ARG
                                                                    |
                                                                    SH $BK_1$ ANTAGONIST MONOMERS

CP-0254: $_D$ARG—ARG—PRO—HYP—GLY—PHE—CYS—$_D$PHE—LEU
                                                                    |
                                                                    SH

CP-0268: $_D$ARG—ARG—PRO—HYP—GLY—PHE—CYS—$_D$(Tic)—Oic
                                                                    |
                                                                    SH $BK_1$/$BK_2$ ANTAGONIST BSH HETERODIMERS

CP-0273: $_D$ARG—ARG—PRO—HYP—GLY—PHE—CYS—$_D$PHE—LEU
                                                                    |
                                                                    (BSH)
                                                                    |
         $_D$ARG—ARG—PRO—HYP—GLY—PHE—CYS—$_D$PHE—LEU—ARG

CP-0272: $_D$ARG—ARG—PRO—HYP—GLY—PHE—CYS—$_D$PHE—LEU
                                                                    |
                                                                    (BSH)
                                                                    |
         $_D$ARG—ARG—PRO—HYP—GLY—PHE—CYS—$_D$(Tic)—Oic—ARG

CP-0290: $_D$ARG—ARG—PRO—HYP—GLY—PHE—CYS—$_D$(Tic)—Oic
                                                                    |
                                                                    (BSH)
                                                                    |
         $_D$ARG—ARG—PRO—HYP—GLY—PHE—CYS—$_D$PHE—LEU—ARG

-continued

CP-0291: DARG—ARG—PRO—HYP—GLY—PHE—CYS—D(Tic)—Oic
                                      |
                                     (BSH)
                                      |
        DARG—ARG—PRO—HYP—GLY—PHE—CYS—D(Tic)—Oic—ARG

By using these heterodimers, it is possible for each "side" of the dimer to act on its respective receptor, i.e., the $BK_1$ antagonist side will block the $BK_1$ receptor and the $BK_2$ antagonist will block the $BK_2$ receptors. This is illustrated in the following.

EXAMPLE 10

Several heterodimers were assessed for their antagonist activity against BK in rat uterus ($BK_2$-receptor) or against des-$Arg^9$-BK ($BK_1$-receptor selective agonist) on rabbit aorta ($BK_1$-receptor) in vitro. Potency in the rat uterus assay was assessed as described above and $pA_2$ values determined. These are shown in Table G.

Potency in rabbit aorta was assessed in the following way: Concentration effect curves were constructed to des-$Arg^9$-BK 1 hour and 3 hours after setting up the preparations. At 5 hours, a single concentration ($10^{-7}M$) of of des-$Arg^9$-BK was added to produce a sustained contraction. Each antagonist was then added, in a cumulative fashion, on top of the contraction and the negative log of the molar concentration of the antagonist causing a 50% reversal ($IC_{50}$) of the concentration measured. These data are also shown in Table G.

TABLE G

| BK₁An/BK₂An MONOMERS, HOMO DIMERS AND HETERODIMERS | | |
|---|---|---|
| COMPOUND # | $BK_2$ RAT UTERUS $pA_2$ | $BK_1$ RABBIT AORTA $IC_{50}$ |
| MONOMERS | | |
| CP-0126 | 7.1 ± 0.1 | Inactive |
| CP-0185 | 10.7 ± 0.9 | 4.1 ± 0.2 |
| CP-0254 | Inactive | 6.4 ± 0.1 |
| CP-0268 | 6.0 | 6.3 ± 0.1 |
| DIMERS | | |
| CP-0127 | 8.5 ± 0.2 | Inactive |
| CP-0273 | 8.2 ± 0.1 | 5.7 ± 0.1 |
| CP-0272 | 8.1 ± 0.2 | 5.9 ± 0.1 |
| CP-0291 | 8.0 ± 0.2 | 6.2 ± 0.1 |

It is clear from the data in Table G that each part of the heterodimer can act independently from the other on its respective receptor. This may enables the treatment of disorders in which both $BK_1$ and $BK_2$ receptors are believed to play a role.

The data presented in Table G also show that while $BK_1/BK_2$ antagonist heterodimers can be synthesized, the resulting activity for each of the geminal ligands is different than that of either the homodimers or the reference monomers. This indicates that at least some of the improvement in the activity of the dimers (homo- or hetero-) may be attributable to the linking element and that the investigation of optimal linker position and chemistry can be explored for each of the geminal ligands independently by the synthesis and testing of linker-modified monomers. Examples of compounds made and tested on this basis are described in Example 11 below.

EXAMPLE 11

Study of linker chemistry using modified monomers:

To optimize linker chemistry prior to the synthesis of a desired homo- or heterodimer, it is preferable to screen a series of linkers using a single reference ligand without having to make and purify dimeric compounds. Illustrated below (Table H) is a series of modified $BK_2$ antagonist monomers formed from the reference ligand CP-0126 and various modifiers serving to approximate the chemistry of one of the geminal ligands plus the linker for use in homo- or hetero-dimeric constructs. Included in this series are a variety of mono-malemidoalkane modified compounds that can be compared to their corresponding homodimers described previously.

TABLE H

| COMPOUND NUMBER | STRUCTURE | RAT UTERUS $pA_2$ | % RECOVERY |
|---|---|---|---|
| CP-0126 | DARG—ARG—PRO—HYP—GLY—PHE—CYS—DPHE—LEU—ARG<br>                                                                                     |<br>                                                                                    X<br>X = SH | 7.1 | 100 |

TABLE H-continued

| COMPOUND NUMBER | STRUCTURE | RAT UTERUS pA$_2$ | % RECOVERY |
|---|---|---|---|
| CP-0139 | 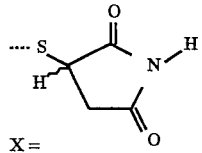<br>X = Racemic Mixture | 7.9 | 100 |
| CP-0264 | 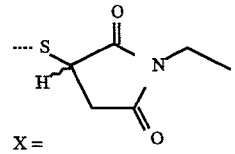<br>X = Racemic Mixture | 7.5 | 100 |
| CP-0257 | 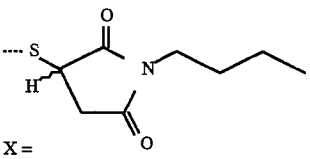<br>X = Racemic Mixture | 8.4 | 80 |
| CP-0174/0175 | 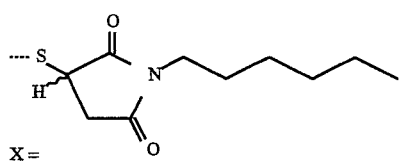<br>X = Racemic Mixture | 8.8 | 50 |
| CP-0256 | 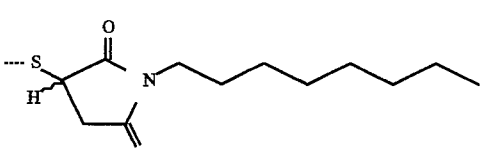 | 9.2 | 0 |
| CP-0266 | 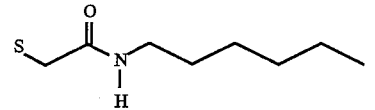 | 8.2 | 70 |
| CP-0174 | 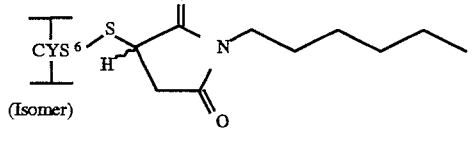<br>(Isomer) | 8.4 | 50 |
| CP-0175 | 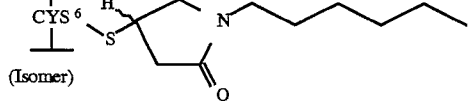<br>(Isomer) | 8.5 | 30 |

The modified monomers shown in Table H comprising S-(N-alkylsuccinimido)-L-cysteine derivatives of CP-0126, were prepared as follows:

To a mixture of CP-0126 (1 eq) and N-alkylmaleimide (1.5 eq) in DMF (ca. 21 mL per mmole of peptide) was added 10 volumes of PBS (pH 7.5). The reaction mixture was stirred overnight at room temperature (monitored periodically by analytical reverse-phase HPLC) and the resulting S-(N-alkylsuccinimido)-modified peptide purified by preparative reverse-phase HPLC. Lyophilization then afforded the pure peptide in 60–80% yield as a fluffy, white solid. Derivatives of CP-0126 prepared by this general procedure include: CP-0139, 264, 257, 174, 175, 256 and 266. Characterization (mass spectral) data for these peptides are shown in Table I.

TABLE I

Mass Spectral Characterization of Cysteine-modified Derivatives of CP-0126

| COMPOUND NUMBER | STRUCTURE | CALC. FW | m/e VALUE[a] |
|---|---|---|---|
| CP-0126 | D—ARG—ARG—PRO—HYP—GLY—PHE—CYS—D—PHE—LEU—ARG<br>                                                |<br>                                                X<br>X = SH | 1264 | NT[b] |
| CP-0139 | 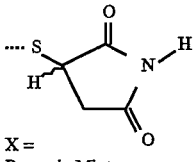<br>X = Racemic Mixture | 1361 | 1361 |
| CP-0264 | 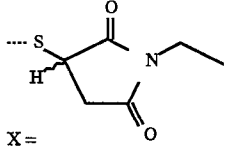<br>X = Racemic Mixture | 1389 | 1389 |
| CP-0257 | 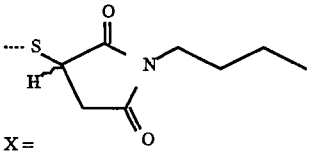<br>X = Racemic Mixture | 1417 | 1417 |
| CP-0174/0175 | 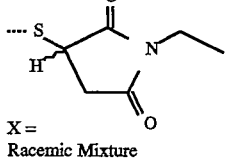<br>X = Racemic Mixture | 1445 | NT[b] |
| CP-0256 | 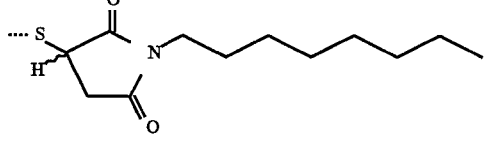 | 1473 | 1473 |
| CP-0266 | 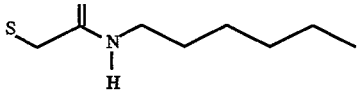 | 1420 | 1420 |
| CP-0174 | 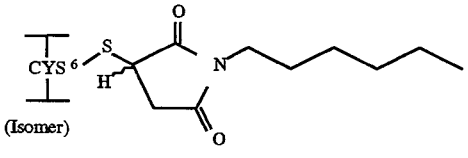<br>(Isomer) | 1445 | 1445 |
| CP-0175 | 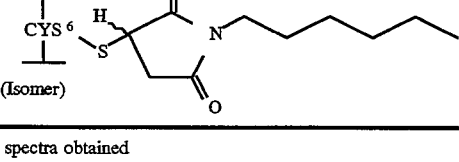<br>(Isomer) | 1445 | 1445 |

[a] Electrospray or plasma desorption mass spectra obtained
[b] Not tested

The data in Table H indicate that, in general, the pA$_2$ of a given monomer increases with increasing alkyl chain length and correlates well with the pA$_2$ of its corresponding homodimer. The data also show that S-(N-alkylsuccinimido)-cysteine modified monomers are more potent than the S-(N-hexylacetamido)-cysteine hexylacetamido)-cysteine modified monomer. Additionally, the results indicate that racemic mixtures as well as the individual optical isomers are both functionally useful with the possibility that racemic mixtures may be preferred in offering a heterogeneity of receptor interaction.

While the data in Table H indicate that even though modified monomers are themselves effective and suitable for use according to the invention, it is usually preferred to use dimers or higher "mers" (homo- or hetero-) because the latter, generally speaking, show an even greater degree of activity over the unmodified peptide monomer, than the corresponding linker-modified monomer. It will also be appreciated that heterodimers capable of interacting with different receptor populations will be categorically different in activity and utility than any given modified monomer.

Just as it is possible to more efficiently explore linker chemistry suitable for inclusion in a desired homo- or hetero-dimeric construct using a single reference ligand and a series of different modifiers, it is also possible to examine a series of potentially desirable geminal ligands with a restricted number of representative modifiers for the purpose of most effectively optimizing homo- and heterodimeric constructs. One such series of modified BK$_1$ antagonist monomers is shown in Example 12 with the results so obtained being illustrated in graphical form in FIG. 7.

EXAMPLE 12

This example illustrates the preparation of S-(N-hexylsuccinimido)-L-cysteine analogs of CP-0298 where the S-(N-hexylsuccinimido) moiety is moved along the peptide chain by varying the position of Cys from 0 to 8.

To a mixture of Cys-containing BK$_1$ peptide antagonist (1 eq) and N-hexylmaleimide (1.5 eq) in DMF (ca. 21 mL per mmole of peptide) was added 10 volumes of 0.1M NH$_4$HCO$_3$ (pH 8). The reaction mixture was stirred overnight at room temperature (monitored periodically by analytical reverse-phase HPLC) and the resulting S-(N-hexylsuccinimido)-L-cysteine analog of CP-0298 purified by preparative reverse-phase HPLC. Lyophilization then afforded the pure peptide in 60–80% yield as a fluffy, white solid. Analogs of CP-0298 prepared by this general procedure include: CP-0311, 322, 324, 326, 328, 307, 305, 309 and 313. Characterization (mass spectral) data for these peptides are shown in Table J.

TABLE J

Mass Spectral Characterization of S-(N-Hexylsuccinimido)$^a$-L—Cysteine Analogs of CP-0298

| COMPOUND NUMBER | STRUCTURE | CALC. FW | m/e$^b$ VALUE |
|---|---|---|---|
| CP-0298 | Lys$^0$—Arg$^1$—Pro$^2$—Pro$^3$—Gly$^4$—Phe$^5$—Ser$^6$—Pro$^7$—Leu$^8$ | 978 | 978 |
| CP-0311 | Cys$^0$—S-(N-hexylsuccinimido)-CP-0298 | 1154 | 1154 |
| CP-0322 | Cys$^1$—S-(N-hexylsuccinimido)-CP-0298 | 1126 | 1126 |
| CP-0324 | Cys$^2$—S-(N-hexylsuccinimido)-CP-0298 | 1185 | 1185 |
| CP-0326 | Cys$^3$—S-(N-hexylsuccinimido)-CP-0298 | 1185 | 1185 |
| CP-0328 | Cys$^4$—S-(N-hexylsuccinimido)-CP-0298 | 1225 | 1225 |
| CP-0307 | Cys$^5$—S-(N-hexylsuccinimido)-CP-0298 | 1134 | 1134 |
| CP-0305 | Cys$^6$—S-(N-hexylsuccinimido)-CP-0298 | 1193 | 1194 |
| CP-0309 | Cys$^7$—S-(N-hexylsuccinimido)-CP-0298 | 1185 | 1185 |
| CP-0313 | Cys$^8$—S-(N-hexylsuccinimido)-CP-0298 | 1169 | 1169 |

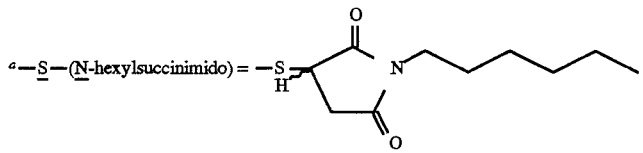

$^a$—S—(N-hexylsuccinimido) = (structure shown)

$^b$Electrospray mass spectra obtained

Figure 7:
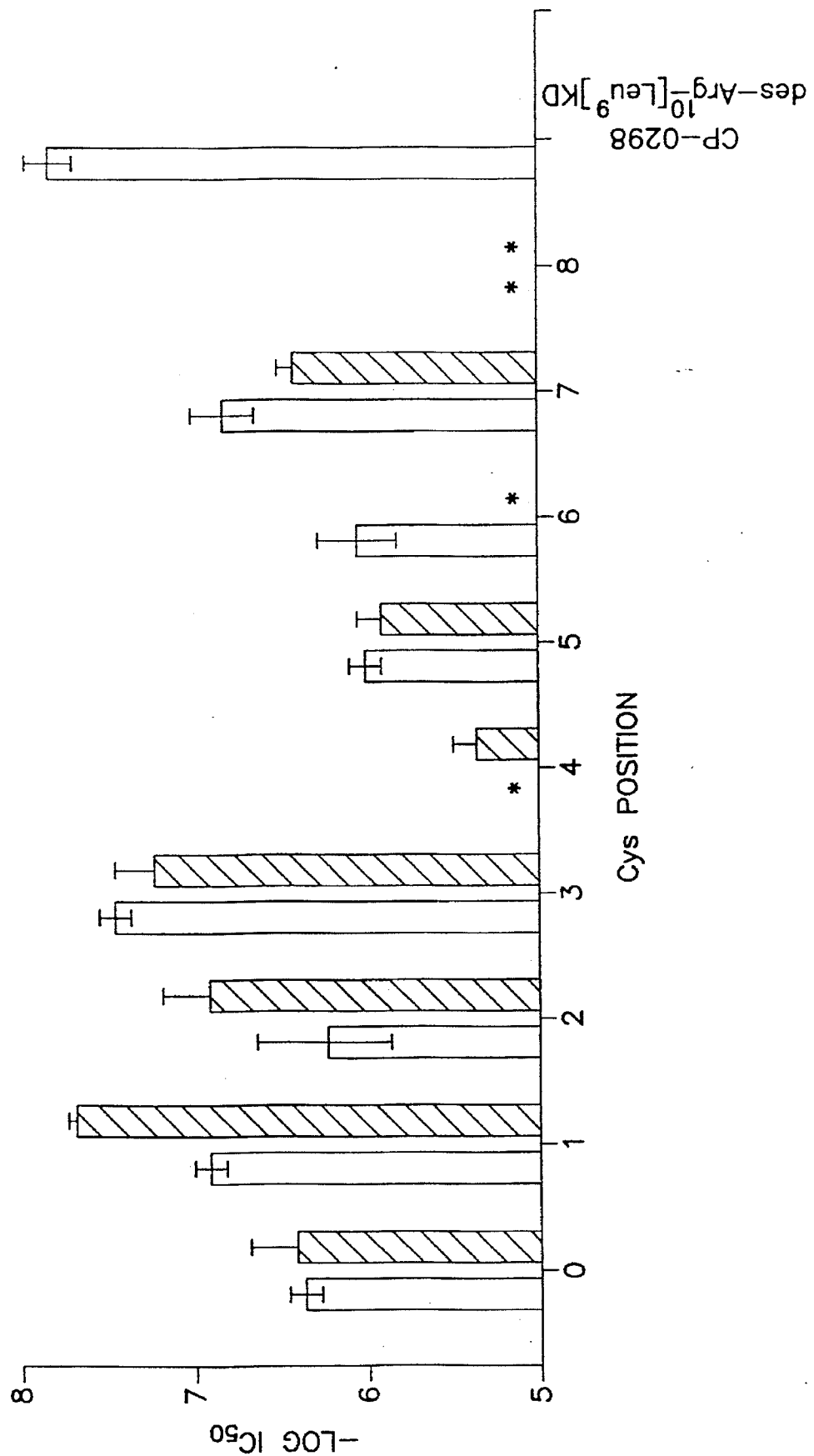
FIG. 7. Shows a comparison of potencies of the reference ligand des $ARG^9$-[$LYS^0$, $LEU^8$]-BK(CP-0298, n=6) with the corresponding series of S-(N-hexylsuccinimido)cycsteine-substituted modified monomers (n=3) on the rabbit aorta in vitro. $K^0$-$R^1$-$P^2$-$G^4$-$F^5$-$S^6$-$P^7$-$L^8$. Open bare are without modifier and filled bars are with modifier. Asterisk denotes $IC50>10^{-5}M$.

The potencies of CP-0298 as the reference ligand and the analogs thereof shown in Table J were compared in vitro in the rabbit aorta assay, the results being graphically shown in FIG. 7.

A number of important points can be made from the data provided by Examples 11 and 12 including the fact that by using the modified monomer approach one can quickly obtain important information with regards to both the preferred type of linking chemistry as well as the preferred position from which to form the desired homo- or heterodimer. Just as in the case of the BK$_2$ series of homodimers, there is a profound effect of linker/modifier position on the activity of the resulting BK$_1$ compound. Interestingly, the modifier position-activity relationship of the BK$_1$ antagonist series of compounds illustrated in FIG. 7 is significantly different than that for the linker position-activity relationship found for the BK$_2$ antagonist series of homodimers. This is perhaps most evident when one compares the effect of modifying or linking the corresponding reference ligand at the "6" position. In the BK$_2$ antagonist homodimer and modified monomer series of compounds, this position was found to be the preferred position for both enhancing activity and improving the duration of action of the resulting compounds. In the BK$_1$ series, however, the homologous position is, in fact, one of the least preferred positions at which to make similar modifications.

EXAMPLE 13

$BK_2$ Antagonist/$BK_1$ Antagonist Heterodimers ($BK_2An/BK_1An$)

This example discloses a series of $BK_2An/BK_1An$ heterodimers that were synthesized and tested on the basis of the structure activity relationships described in Example 12. Table K is a listing of representative monomers used in these studies, their structures, and their potencies as measured in the rabbit aorta assay for $BK_1$ receptor-mediated activity. Table L is a tabulation of representative $BK_2An/BK_1An$ heterodimers derived from these monomers illustrating the ability to make potent, dually active compounds based on the principles disclosed in the previous example.

were added and the dimerization allowed to proceed for ca. 1 hour at room temperature. The resulting Cys-(bissuccinimidohexane)-Cys peptide dimer was purified by preparative reverse-phase HPLC and lyophilized to yield a white, fluffy solid. Overall yields ranged from 40–50%. Heterodimers prepared by this general procedure include: CP-0273, 364, 365, 386, 382 and 383 as shown in Table L.

TABLE K

| | $BK_1$ RECEPTOR ANTAGONIST MONOMERS | | |
|---|---|---|---|
| COMPOUND # | STRUCTURE POSITION<br>0—1—2—3—4—5—6—7—8—9 | $BK_2$<br>(RAT UTERUS)<br>$pA_2$ | $BK_1$<br>(RABBIT AORTA)<br>$IC_{50}$ |
| CP-0298 | K—R—P—P—G—F—S—P—L | Inactive | 7.9 ± 0.1 |
| CP-0253 | $_D$R—R—P—J—G—F—S—$_D$F—L | Inactive | 6.9 ± 0.1 |
| CP-0254 | $_D$R—R—P—J—G—F—C—$_D$F—L | Inactive | 6.4 ± 0.1 |
| CP-0267 | $_D$R—R—P—J—G—F—S—$_D$Tic—Oic | 5.7 ± 0.1 | 7.5 ± 0.2 |
| CP-0345 | $_D$R—R—P—J—G—Thi—S—$_D$Tic—Oic | 7.6 ± 0.4 | 7.1 ± 0.1 |
| CP-0362 | $_D$R—C—P—J—G—F—S—P—L | Inactive | 6.0 ± 0.2 |
| CP-0363 | $_D$R—C—P—J—G—F—S—$_D$Tic—Oic | Inactive | 6.2 ± 0.3 |
| CP-0374 | K—C—P—J—G—F—S—P—L | Inactive | 6.5 ± 0.3 |
| CP-0375 | K—C—P—P—G—Thi—S—P—L | Inactive | 6.5 ± 0.3 |
| CP-0376 | $_D$R—C—P—J—G—F—S—$_D$F—L | Inactive | 4.9 ± 0.3 |
| CP-0388 | $_D$R—K—P—J—G—F—S—P—L | Inactive | 6.5 ± 0.1 |

The Cys-(bissuccinimidohexane)-Cys $BK_2/BK_1$ antagonist heterodimers referred to in Table L were prepared as follows:

To a mixture of CP-0126 (1 eq) and bismaleimidohexane (BMH, 2 eq) in DMF (ca. 21 mL per mmole of peptide) was added 10 volumes of 0.1M $NH_4HCO_3$ (pH 8). The reaction mixture was stirred at room temperature for ca. 1 hour (monitored periodically by analytical reverse-phase HPLC) and the resulting S-(N-hexylmaleimido)succinimido-derivative of CP-0126 purified by preparative reverse-phase. HPLC. The resulting peptide, isolated in approximately 70% yield after lyophilization, was then combined with a Cys-containing $BK_1$ peptide antagonist (1.5 eq) in DMF (same mL/mmole as specified above). Ten volumes of 0.1M $NH_4HCO_3$ (pH 8)

TABLE L

| | $BK_1An/BK_2An$ HETERODIMERS | | |
|---|---|---|---|
| COMPOUND# | STRUCTURE | $BK_2$<br>Rat Uterus<br>$pA_2$ | $BK_1$<br>Rabbit Aorta<br>$IC_{50}$ |
| CP-0273 | CP-0126-(BSH)$^a$-CP-0254 | 8.2 ± 0.1 | 5.7 ± 0.1 |
| CP-0364 | CP-0126-(BSH)$^a$-CP-0362 | 8.3 ± 0.2 | 7.5 ± 0.1 |
| CP-0365 | CP-0185-(BSH)$^a$-CP-0363 | 8.4 ± 0.1 | 7.4 ± 0.5 |
| CP-0386 | CP-0126-(BSH)$^a$-CP-0376 | 7.6 ± 0.1 | 7.1 ± 0.2 |
| CP-0389 | CP-0126-(ESC)$^b$-CP-0388 | 7.4 ± 0.1 | 6.5 ± 0.1 |
| CP-0382 | CP-0126-(BSH)$^a$-CP-0374 | Agonist | 6.2 ± 0.3 |
| CP-0383 | CP-0126-(BSH)$^a$-CP-0375 | Agonist | 7.8 ± 0.1 |

$^a$BSH = bissuccinimidohexane
$^b$ESC = epsilon succinimido n-caproyl

Characterization (mass spectral) data for these peptides are shown in Table M.

TABLE M

MASS SPECTRAL CHARACTERIZATION OF BK₂An/BK₁An HETERODIMERS

| COMPOUND NUMBER | STRUCTURE | CALC. FW | (M + H) VALUE[c] |
|---|---|---|---|
| CP-0273 | CP-0126-(BSH)[a]-CP-0254 | 2647 | 2648 |
| CP-0364 | CP-0126-(BSH)[a]-CP-0362 | 2529 | 2530 |
| CP-0365 | CP-0185-(BSH)[a]-CP-0363 | 2681 | 2682 |
| CP-0386 | CP-0126-(BSH)[a]-CP-0376 | 2579 | 2580 |
| CP-0389 | CP-0126-(ESC)[b]-CP-0388 | 2470 | 2471 |
| CP-0382 | CP-0126-(BSH)[a]-CP-0374 | 2502 | 2503 |
| CP-0383 | CP-0126-(BSH)[a]-CP-0375 | 2492 | 2493 |

[a]BSH = bissuccinimidohexane
[b]ESC = epsilon succinimido n-caproyl
[c]Plasma desorption mass spectra obtained In vitro screening:

Compounds CP-0273 and CP-0386 were selected for comparison purposes because these heterodimers use the same $BK_2$ antagonist ligand (CP-0126) and the same linker (BSH) with two geminal ligands (CP-0254 and CP-0376) that differ only in the position of dimerization. The former compound is dimerized at the "6" position on both sides of the dimer (the most preferred and least preferred positions for $BK_2$ and $BK_1$ antagonists, respectively) while the latter compound utilizes the most preferred positions for each of the geminal ligands as determined by modified monomer analysis (positions "6" and "1", respectively). As will be appreciated from the data (Table L), the potencies of the two compounds with respect to $BK_2$ receptor antagonism are identical within the experimental error of the assay system while their $BK_1$ antagonist activities are almost 100 fold different, as predicted by their respective modified monomers.

It should be noted that the use of the modified monomer as the sole predictor of activity with regards to the receptor specific activity of the heterodimer has its limitations. These limitations further illustrate the importance of the interactions of the geminal ligand with the ligand in question in determining the final activity of the dimeric construct. Examples of the importance of this interaction are compounds CP-0382 and CP-0383 wherein $BK_1$ antagonism was retained but $BK_2$ activity was changed from strict antagonism to substantial partial agonism. The $BK_1$ antagonist ligands (CP-0374 and CP-0375) when tested as monomers had no measurable activity either as agonists or antagonists in the rat uterus $BK_2$ receptor system. This categorical shift in activity of the geminal ligand can only be attributable to the effects on the overall dimer caused by the linker and ligands tested and clearly illustrates the importance and potential utility of dimeric constructs in general.

In vivo analysis:

That heterodimeric constructs block the activities attributable to two different receptor populations simultaneously when administered to an intact animal has been known using a standard assay of $BK_2$ and $BK_1$ receptor activity (see, deBlois, Bouthillier, and Marceau, Brit. J. Pharm., 103, 1057–1066, 1991). In normal rabbits, no changes in systemic arterial blood pressure can be detected in response to challenges with $BK_1$ receptor agonists. There is, however, a predictable and reproducible response to $BK_2$ agonists constituatively present. After stimulation with LPS $BK_1$ receptor activity will develop over time such that profound responses to doses of $BK_1$ agonists that were previously inconsequential in nature are observed after a 3–4 hour period. Responses to $BK_2$ agonists are unchanged in these animals. At this point, one can test directly the ability to block both $BK_1$ and $BK_2$ mediated reductions in systemic blood pressure simultaneously with a heterodimeric antagonist.

FIGS. 8a, b and c comprise actual blood pressure traces from a series of experiments designed to illustrate the ability of a representative heterodimer (CP-0364) to block both $BK_1$- and $BK_2$- mediated hypotensive responses simultaneously. FIG. 8a is the blood pressure response profile of a group of normal rabbits after endotoxin pre-treatment to $BK_1$ and $BK_2$ agonists delivered as intravenous bolus injections in the absence and presence of the $BK_2$ antagonist CP-0088, FIG. 8b illustrates the response profiles of similar groups of animals in the presence of the selective $BK_1$ antagonist CP-0298, Finally, FIG. 8c is the response profile of a group of similarly treated animals to $BK_1$ and $BK_2$ agonists in the absence and presence of the $BK_2An/BK_1An$ heterodimer CP-0364, As can be seen from these traces, the selective antagonists will only affect the responses to their respective agonists while the heterodimer is capable of blocking the response profile to both agonists simultaneously. This does not imply that any given heterodimer molecule is engaging receptors of two different classes simultaneously but that the population of heterodimer molecules can antagonize both populations of $BK_1$ and $BK_2$ receptors in the same animals at the same time. Data from a representative group of monomers, homodimers and heterodimers is summarized in Table N.

Figure 8:
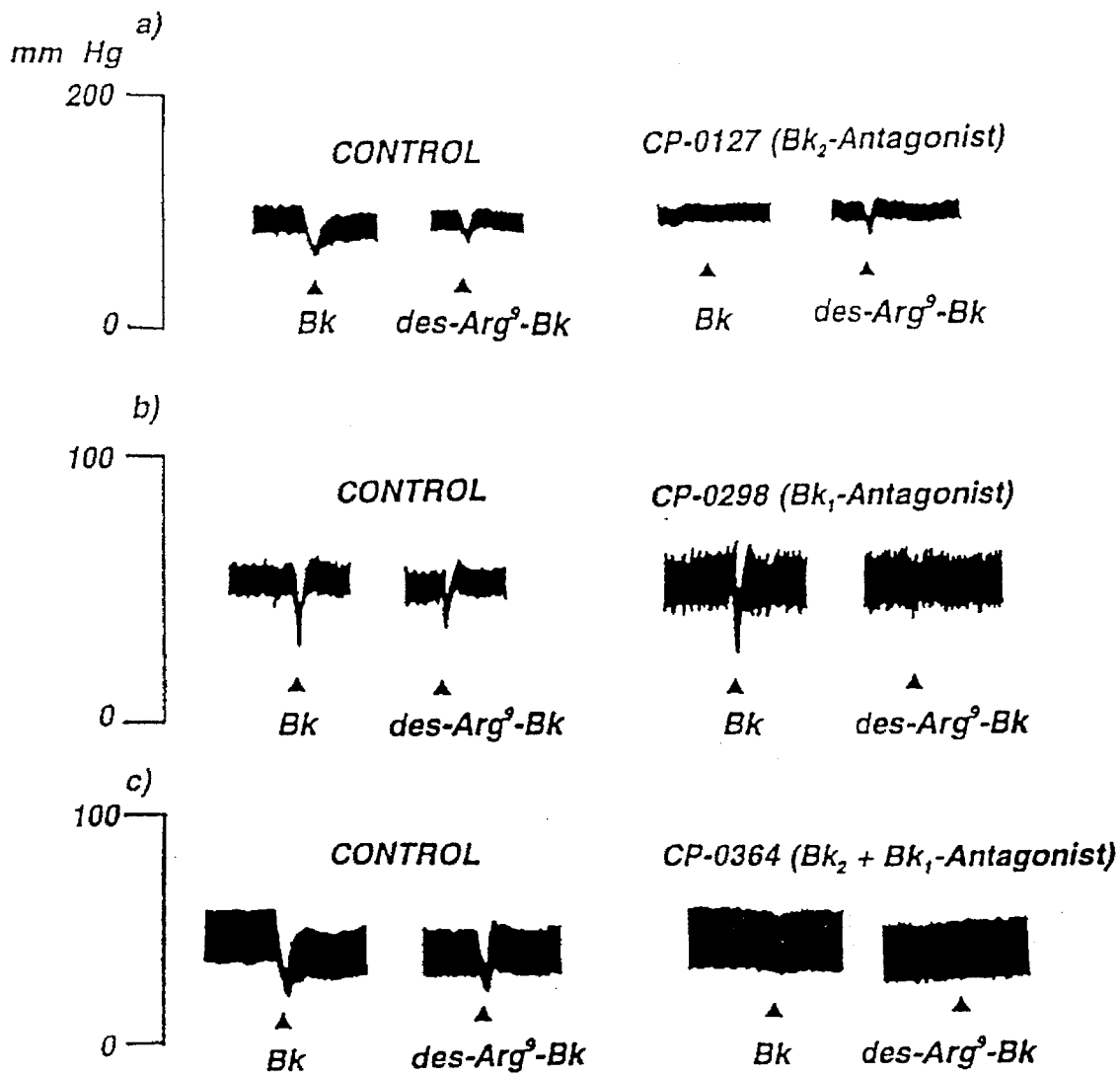
FIG. 8a. Blood pressure response profile of a group of normal rabbits after endotoxin pretreatment to $BK_1$ and $BK_2$ agonists delivered as intravenous bolus injections in the absence and presence of the $BK_2$ antagonist CP-0088.
FIG. 8b. Response profiles of similar groups of animals in the presence of the selective $BK_2$ antagonist CP-0298.
FIG. 8c. Response profile of a group of similarly treated animals to $BK_1$ and $BK_2$ agonists in the absence and presence of the $BK_2An/BK_1$ heterodimer CP-0364.

The expected antagonist activity is based on the data summarized in Tables K and L. The in vivo experimental data reported are qualitative measurements of antagonist activity at three different doses (1, 3 and 10 µg $kg^{-1}$ $min^{-1}$) in rabbits given a sub-lethal dose of LPS (10 µg), 20 hours before initiation of the experiment. The symbol "+" indicates complete blockade of the blood pressure response to the appropriate agonist (as seen in FIG. 8), while "±" indicates partial blockade and "−" indicates no observable effect at the dose indicated. It is clear from these data that the in vitro characterization of the antagonist activity of these compounds is a relatively accurate measure of their in vivo activity and is a useful technique for screening heterodimer for their desired activity.

TABLE N

IN VIVO ACTIVITY OF VARIOUS MONOMERS HOMODIMERS AND HETERODIMERS

| | EXPECTED | OBSERVED ANTAGONIST ACTIVITY | | | | | |
|---|---|---|---|---|---|---|---|
| | | $BK_1$ | | | $BK_2$ | | |
| COMPOUND | ANTAGONIST ACTIVITY | 1 | 3 | 10 | 1 | 3 | 10 |
| CP-0088 | $BK_2$ | − | − | − | + | + | + |
| CP-0126 | $BK_2$ | − | − | − | + | + | + |
| CP-0127 | $BK_2$ | − | − | − | + | + | + |
| CP-0184 | $BK_2$ | − | − | − | + | + | + |
| CP-0298 | $BK_1$ | + | + | + | − | − | − |
| CP-0267 | $BK_1/BK_2$ | − | − | + | − | − | +/− |
| CP-0345 | $BK_1/BK_2$ | − | + | + | − | +/− | + |
| CP-0364 | $BK_1/BK_2$ | + | + | + | + | + | + |
| CP-0365 | $BK_1/BK_2$ | − | + | + | − | + | + |
| CP-0386 | $BK_1/BK_2$ | + | + | + | + | + | + |

As noted earlier, a further embodiment of the invention is the provision of compounds of Formula (III):

(Y)(X)(BKA)

where X and BKA have the meanings given earlier and Y represents a peptide chain which demonstrates antagonist or agonist activity with respect to a non-BK receptor, i.e. heterodimers targeted to BK (e.g. $BK_2$) and non-BK receptor populations. Since it has been shown above that $BK_1$/$BK_2$ antagonist heterodimers according to the invention can provide effective dual activity directed to both types of receptors, it will be appreciated that other potent heterodimers can be prepared following the present disclosure and teachings. This may be particularly important in the case where there is a close relationship between the activities involved.

It is known that in a number of pathophysiologically important processes there is an intimate interaction of inflammatory and neurogenic mediators. This occurs, for example, in both pain secondary to tissue trauma (accidental and post-operative) as well as in asthma. In both situations there is a complex interplay of tissue and plasma derived mediators (kinins acting at $BK_2$ receptors) and neuronally derived factors such as substance P ($NK_1$ receptors) and neurokinin A ($NK_2$ receptors). Finally, there are locally acting neuronal receptors of the μ-opioid class that, when stimulated can inhibit the release of the neurogenic peptides regardless of type (substance P, neurokinin A, neurokinin B, cholecystokinin, CGRP etc.).

Given the interaction of these as well as other inflammatory and neurogenic mediators, no one agent is likely to be universally efficacious in ameliorating the symptoms attendant to the pathophysiology. However, heterodimers according to the invention should be particularly useful in addressing these problems with single agents possessing dual selectivity. In addition, it appears that heterodimers according to the invention can be used to circumvent a number of heretofore limiting problems confronting the development of uniquely selective agents. For example, as in the case for BK antagonists, substance P and neurokinin A antagonists as well as μ-opioid agonist peptides all share the common problem of rapid inactivation by a number of tissues associated as well as soluble endo- and exopeptidases. It is believed that the present heterodimers offer a way in which rapid inactivation can be prevented without sacrificing both potency as well as specificity as found for the $BK_2$ homodimers described herein. Enkephalin or opioid agonists have an additional problem in that they have considerable abuse or dependency potential as well as limiting mental and cognitive side effects if they gain access to the central nervous system. Again, it is believed that heterodimers should allow for adequate, if not exceptional, peripheral activity without the unwanted and limiting central nervous system side effects by virtue of the fact that the μ-opioid receptor agonist will be covalently linked to a highly cationic BK antagonist which is unlikely to penetrate the blood brain barrier to any significant extent.

The examples which follow describe various heterodimers formed by the dimerization of the reference $BK_2$ ligand, CP-0126, with a variety of $NK_1$ and $NK_2$ antagonists as well as a series of μ-opioid agonist peptides. As will be obvious to those skilled in the art, the design, synthesis and use of such heterodimers is not in any way limited to the specific compounds illustrated in this disclosure, but may be accomplished by pairing any two of a multitude of appropriate ligands using standard chemistries and without undue experimentation.

EXAMPLE 14

$BK_2$ Antagonist/$NK_1$ Antagonist Heterodimers ($BK_2An$/$NK_1An$)

In order to illustrate the potential of blocking two different receptor populations with a single compound a consensus $NK_1$ receptor antagonist (DArg-DPro-Lys-Pro-Gln-Asn-DPhe-Phe-DTrp-Leu-Nle) was synthesized. This antagonist was found to have a $pA_2$ of 5.6 when tested against substance P in a standard guinea pig ileum assay of $NK_1$ receptor activity. Once the activity of this reference ligand was established, a series of lysine containing monomers formed by the systematic substitution of a lysine residue sequentially through the reference peptide was synthesized. These compounds were then linked to CP-0126 using the heterobifunctional linking agent: epsilon maleimido n-caproyl N-hydroxysuccinimide ester (EMCS), forming a series of epsilon succinimido n-caproyl (ESC) heterodimers (Table O).

TABLE O $BK_2An$/$NK_1An$ HETERODIMERS

| COMPOUND | STRUCTURE | $NK_1$:GPI $pA_2$ (± s.e.m.) | $BK_2$:RU $pA_2$ (± s.e.m.) |
| --- | --- | --- | --- |
| CP-0390 | CP-0126-(ESC)$^a$-LYS$^1$[CT-0008]$^b$ | 4.8 ± 0.2 | 7.2 ± 0.2 |
| CP-0391 | CP-0126-(ESC)$^a$-LYS$^2$[CT-0008]$^b$ | 5.0 ± 0.1 | 7.1 ± 0.2 |
| CP-0392 | CP-0126-(ESC)$^a$-LYS$^3$[CT-0008]$^b$ | 5.3 ± 0.1 | 7.0 ± 0.2 |
| CP-0393 | CP-0126-(ESC)$^a$-LYS$^4$[CT-0008]$^b$ | 5.5 ± 0.2 | 7.4 ± 0.1 |
| CP-0394 | CP-0126-(ESC)$^a$-LYS$^5$[CT-0008]$^b$ | 5.8 ± 0.3 | 7.9 ± 0.1 |
| CP-0395 | CP-0126-(ESC)$^a$-LYS$^6$[CT-0008]$^b$ | 6.3 ± 0.1 | 7.3 ± 0.1 |
| CP-0396 | CP-0126-(ESC)$^a$-LYS$^7$[CT-0008]$^b$ | Inactive | 8.0 ± 0.1 |
| CP-0397 | CP-0126-(ESC)$^a$-LYS$^8$[CT-0008]$^b$ | Inactive | 7.7 ± 0.2 |
| CP-0398 | CP-0126-(ESC)$^a$-LYS$^9$[CT-0008]$^b$ | Inactive | 6.4 ± 0.2 |
| CP-3099 | CP-0126-(ESC)$^a$-LYS$^{10}$[CT-0008]$^b$ | 4.9 ± 0.2 | 7.4 ± 0.1 |
| CP-0400 | CP-0126-(ESC)$^a$-LYS$^{11}$[CT-0008]$^b$ | Inactive | 7.6 ± 0.3 |

$^a$ESC = epsilon succinimido n-caproyl
$^b$CT-0008 = D—Arg—D—Pro—Lys—Pro—Gln—Asn—D—Phe—Phe—D—Trp—Leu—Nle—$CONH_2$ The Cys-(epsilon succinimido n-caproyl)-Lys $BK_2An$/$NK_1An$ heterodimers shogun in Table O were prepared as follows:

To a preparation of L-Lys(FMOC)-containing $NK_1$ peptide antagonist-resin (MBHA, 0.5 mmole peptide) was added 50% piperidine in DMF (ca. 20 mL). The resulting mixture was bubbled gently with $N_2$ (g) for 20 minutes to afford complete removal of the (Lys)FMOC protecting group and then the peptide-resin was washed well with DMF. The peptide-resin was resuspended in DMF and 1.5 eq of EMCS (epsilon maleimido n-caproic acid N-hydroxysuccinimide ester) was added. The acylation reaction was allowed to proceed at room temperature for 2–3 hours (verification of complete acylation accomplished with the Kaiser test) after which time the peptide-resin was washed well with DMF, then with 10% (v/v) $NH_4HCO_3$/ DMF stock concentration: 0.1M, pH8). CP-0126, 3 eq in 10% (v/v) $NH_4HCO_3$/DMF, was added to the maleimido-containing peptide-resin and the subsequent conjugate addition (1,4-addition) allowed to proceed at room temperature for several hours. The peptide-resin was then washed well (successively) with 10% $NH_4HCO_3$/DMF, DMF and dichloromethane. Following extensive drying in vacuo, the heterodimer was deprotected/cleaved from the peptide-resin with anhydrous HF at 0° C. and then purified by preparative reverse-phase HPLC. Lyophilization afforded the pure peptide in 50–60% yield as a fluffy, white solid. Heterodimers prepared by this general procedure include: CP-0390, 391, 392, 393, 394, 395, 396, 397, 398, 399 and 400. Characterization (mass spectral) data for these peptides are shown in Table P.

TABLE P

Mass Spectral Characterization of $BK_2An/NK_1An$ Heterodimers

| COMPOUND NUMBER | STRUCTURE | CALC. FW | $(M + H)^c$ VALUE |
|---|---|---|---|
| CP-0390 | CP-0126-(ESC)$^a$-Lys$^1$[CT-0008]$^b$ | 2874 | 2875 |
| CP-0391 | CP-0126-(ESC)$^a$-Lys$^2$[CT-0008]$^b$ | 2933 | 2934 |
| CP-0392 | CP-0126-(ESC)$^a$-Lys$^3$[CT-0008]$^b$ | 2903 | 2904 |
| CP-0393 | CP-0126-(ESC)$^a$-Lys$^4$[CT-0008]$^b$ | 2933 | 2934 |
| CP-0394 | CP-0126-(ESC)$^a$-Lys$^5$[CT-0008]$^b$ | 2902 | 2903 |
| CP-0395 | CP-0126-(ESC)$^a$-Lys$^6$[CT-0008]$^b$ | 2916 | 2917 |
| CP-0396 | CP-0126-(ESC)$^a$-Lys$^7$[CT-0008]$^b$ | 2883 | 2884 |
| CP-0397 | CP-0126-(ESC)$^a$-Lys$^8$[CT-0008]$^b$ | 2883 | 2884 |
| CP-0398 | CP-0126-(ESC)$^a$-Lys$^9$[CT-0008]$^b$ | 2844 | 2845 |
| CP-0399 | CP-0126-(ESC)$^a$-Lys$^{10}$[CT-0008]$^b$ | 2918 | 2919 |
| CP-0400 | CP-0126-(ESC)$^a$-Lys$^{11}$[CT-0008]$^b$ | 2918 | NT$^d$ |

$^a$ESC = epsilon succinimido n-caproyl
$^b$CT-0008 = D—Arg—D—Pro—Lys—Pro—Gln—Asn—D—Phe—Phe—D—Trp—Leu—Nle—$CONH_2$
$^c$Plasma desorption mass spectra obtained
$^d$NT = Not Tested In connection with the above, it is noted that the maleimido-containing $NK_1$ peptide antagonist can be cleaved from the peptide-resin, purified and then condensed with CP-0126 in solution, if necessary or desired.

It is also important to note that a different linking strategy was employed for this series of compounds in order to further emphasize that cysteine based chemistry is not required for implementation of the invention and to illustrate the breadth of potential chemistries that can be employed in the formation of dimeric structures. As can be seen from the data presented, heterodimers capable of antagonizing both $BK_2$ as well as $NK_1$ receptor activity, while maintaining or improving the activity of the appropriate geminal ligand for its specific receptor, are possible using this type of synthetic strategy. In this example, positions 4, 5 and 6 in the $NK_1$ antagonist geminal ligand appear to be optimal for maintaining or improving both $NK_1$ antagonist as well as $BK_2$ antagonist activity. Obviously, Cys/Cys heterodimers of this type are also possible and may even be preferred for certain applications.

EXAMPLE 15

$BK_2$ Antagonist/$NK_2$ Antagonist Heterodimers ($BK_2An$/ $NK_2An$)

For purposes of illustration and to further demonstrate that $BK_2An$-based heterodimers are capable of effectively blocking two different receptor populations, a series of $BK_2An/NK_2An$ heterodimers were prepared in the manner described above for other heterodimeric structures. In this case, a Cys/Cys linking strategy was employed but it is to be appreciated that a Cys/Lys or alternative strategy could be employed with equal ease.

The Cys-(bissuccinimidohexane)-Cys $BK_2/NK_2$ antagonist heterodimers of the reference ligand CT-0022 (Asp-Tyr-DTrp-Val-DTrp-DTrp-Arg-$CONH_2$) were prepared as follows:

To a mixture of Cys-containing, $BK_2$ peptide antagonist (1 eq) and bismaleimidohexane (BMH, 2 eq) in DMF (ca. 21 mL per mmole of peptide) was added 10 volumes of 0.1M $NH_4HCO_3$ (pH 8). The reaction mixture was stirred at room temperature for several hours (monitored periodically by analytical reverse-phase HPLC) and the resulting S-( N-hexylmaleimido) succinimido-derivative of the $BK_2$ antagonist purified by preparative reverse-phase HPLC. The resulting peptide, isolated in approximately 70% yield after lyophilization, was then combined with CP-0126 (1.5 eq) in DMF (same mL/mmole as specified above). Ten volumes of 0.1M $NH_4HCO_3$ (pH 8) were added and the dimerization allowed to proceed for several hours at room temperature. The resulting Cys-(bissuccinimidohexane)-Cys peptide dimer was purified by preparative reverse-phase HPLC and lyophilized to yield a white, fluffy solid. Overall yields ranged from 40–50%. Heterodimers prepared by this general procedure include: CP-0411, 412, 413, 414, 415, 416 and 417. Characterization (mass spectral) data for these peptides are shown in Table Q.

TABLE Q

Mass Spectral Characterization of $BK_2An/NK_2An$ Heterodimers

| COMPOUND NUMBER | STRUCTURE | CALC. FW | $(M + H)^c$ VALUE |
|---|---|---|---|
| CP-0411 | CP-0126-(BSH)$^a$-Cys$^1$[CT-0022]$^b$ | 2639 | 2640 |
| CP-0412 | CP-0126-(BSH)$^a$-Cys$^2$[CT-0022]$^b$ | 2591 | 2592 |
| CP-0413 | CP-0126-(BSH)$^a$-Cys$^3$[CT-0022]$^b$ | 2568 | 2569 |
| CP-0414 | CP-0126-(BSH)$^a$-Cys$^4$[CT-0022]$^b$ | 2655 | 2656 |
| CP-0415 | CP-0126-(BSH)$^a$-Cys$^5$[CT-0022]$^b$ | 2568 | 2569 |
| CP-0416 | CP-0126-(BSH)$^a$-Cys$^6$[CT-0022]$^b$ | 2568 | 2569 |
| CP-0417 | CP-0126-(BSH)$^a$-Cys$^7$[CT-0022]$^b$ | 2598 | 2598 |

$^a$BSH = bissuccinimidohexane
$^b$CT-0022 = Asp—Tyr—D—Trp—Val—D—Trp—D—Trp—Arg—$CONH_2$
$^c$Plasma desorption mass spectra obtained The heterodimers thus obtained were tested for activity as heretofore described, the results being shown in Table R. In this Table -log [M] represents the negative log of the molar concentration of the antagonist necessary to reduce a sustained contractile response produced by neurokinin A by 50%.

TABLE R

| | BK₂An/NK₂An HETERODIMERS | | |
|---|---|---|---|
| COMPOUND | STRUCTURE | BK$_2$ Rat Uterus pA$_2$ | NK$_2$ Rabbit Pulm Art −log [M] |
| CP-0411 | CP0126-(BSH)$^a$-Cys$^1$[CT-0022]$^b$ | 7.5 ± 0.1 | 5.5 ± 0.3 |
| CP-0412 | CP0126-(BSH)$^a$-Cys$^2$[CT-0022]$^b$ | 7.9 ± 0.1 | Inactive |
| CP-0413 | CP0126-(BSH)$^a$-Cys$^3$[CT-0022]$^b$ | 8.5 ± 0.3 | Inactive |
| CP-0414 | CP0126-(BSH)$^a$-Cys$^4$[CT-0022]$^b$ | 7.8 ± 0.1 | 5.2 ± 0.2 |
| CP-0415 | CP0126-(BSH)$^a$-Cys$^5$[CT-0022]$^b$ | 7.8 ± 0.1 | 5.2 ± 0.1 |
| CP-0416 | CP0126-(BSH)$^a$-Cys$^6$[CT-0022]$^b$ | 8.7 ± 0.2 | 5.6 ± 0.2 |
| CP-0417 | CP0126-(BSH)$^a$-Cys$^7$[CT-0022]$^b$ | 8.0 ± 0.2 | 5.6 ± 0.1 |

$^a$BSH = bissuccinimidohexane
$^b$CT-0022 = Asp—Tyr—D—Trp—Val—D—Trp—D—Trp—Arg—CONH$_2$ The data shown in Table R clearly indicate that, as was the case for the BK$_2$An/BK$_1$An and BK$_2$An/NK$_1$An heterodimers, useful BK$_2$An/NK$_2$An heterodimers are possible. Based on these results and the foregoing, it is evident that other Formula (III) type heterodimers can be prepared as the ligands utilized for the: three series of heterodimeric antagonists illustrated herein are representative of the antagonists reported in the literature.

EXAMPLE 16

This example illustrates the preparation of BK$_2$ antagonist/μ-opioid receptor agonist heterodimers (BK$_2$An/ μAg). While it is clear from the foregoing that antagonist/ antagonist heterodimers are capable of interacting with their respective receptor populations, antagonist/agonist heterodimers can also be prepared which are capable of interacting with their respective receptors as well.

To illustrate this aspect of the invention, a series of monomeric μ-opioid receptor agonists were made in which a carboxy terminal cysteine residue was added to a known inhibitory peptide. These novel antagonists were then linked to CP-0126 with a series of bismaleimidoalkane linkers and tested in a standard assay of μ-opioid receptor activity as well as in the standard BK$_2$ assay system used for the previous heterodimers.

The Cys-(bissuccinimidoalkane)-Cys BK$_2$ antagonist/μ-opioid receptor agonist heterodimers in the example were prepared as follows:

To a mixture of Cys-containing, μ-opioid receptor peptide agonist (1 eq) and bismaleimidoalkane (2 eq) in DMF (ca. 21 mL per mmole of peptide) was added 10 volumes of 0.1M NH$_4$HCO$_3$ (pH 8). The reaction mixture was stirred at room temperature for ca. 1 hour (monitored periodically by analytical reverse-phase HPLC) and the resulting S-( N-alkylmaleimido)succinimido derivative of the μ-opioid receptor agonist purified by preparative reverse-phase HPLC. The resulting peptide, isolated in approximately 70% yield after lyophilization, was then combined with CP-0126 (1.5 eq) in DMF (same mL/mmole as specified above). Ten volumes of 0.1M NH$_4$HCO$_3$ (pH 8) were added and the dimerization allowed to proceed for several hours at room temperature. The resulting Cys-(bissuccinimidoalkane)-Cys peptide dimer was purified by preparative reverse-phase HPLC and lyophilized to yield a white, fluffy solid. Overall yields ranged from 40–50%. Heterodimers prepared by this general procedure include CP-0427 through CP-0432.

Characterization (mass spectral) data for these peptides are shown in Table S.

TABLE S

| Mass Spectral Characterization of BK$_2$An/μ Ag Heterodimers | | | |
|---|---|---|---|
| COMPOUND NUMBER | STRUCTURE | CALC. FW | (M + H)$^d$ VALUE |
| CP-0427 | CP-0126-(BSH)$^a$-CO-0001 | 2200 | 2201 |
| CP-0248 | CP-0126-(BSH)$^a$-CO-0003 | 2101 | 2102 |
| CP-0429 | CP-0126-(BSB)$^b$-CO-0001 | 2172 | 2173 |
| CP-0430 | CP-0126-(BSB)$^b$-CO-0003 | 2073 | 2074 |
| CP-0431 | CP-0126-(BSD)$^c$-CO-0001 | 2283 | 2284 |
| CP-0432 | CP-0126-(BSD)$^c$-CO-0001 | 2184 | 2185 |

$^a$BSH = bissuccinimidohexane
$^b$BSB = bissuccinimidobutane
$^c$BSD = bissuccinimidododecane
$^d$Plasma desorption mass spectra obtained As can be seen from the date in Table T, these types of compounds are also capable of interacting with their respective receptor populations in the predicted manner. Compounds such as these are expected to be useful in the treatment of a number of disease states, including postoperative pain and asthma.

TABLE T

| IN VITRO Activity of BK$_2$AN/μ Ag Heterodimers | | | |
|---|---|---|---|
| COMPOUND | DESCRIPTION | BK$_2$ RAT UTERUS pA$_2$ | μ-OPIOID GUINEA PIG ILEUM IC$_{50}$ |
| CO-0001 | Y—G—G—F—L—C—CONH$_2$ | — | 6.0 ± 0.5 |
| CO-0003 | Y—(DA)—G—F—C—CONH$_2$ | — | 6.8 ± 0.2 |

TABLE T-continued

IN VITRO Activity of $BK_2AN/\mu$ Ag Heterodimers

| COMPOUND | DESCRIPTION | $BK_2$ RAT UTERUS $pA_2$ | μ-OPIOID GUINEA PIG ILEUM $IC_{50}$ |
|---|---|---|---|
| CP-0427 | CO-0001-(BSH)-CP-0126 | 7.6 ± 0.2 | 6.4 ± 0.4 |
| CP-0428 | CO-0003-(BSH)-CP-0126 | 8.3 ± 0.5 | 6.6 ± 0.4 |
| CP-0429 | CO-0001-(BSB)-CP-0126 | 7.6 ± 0.1 | 6.3 ± 0.3 |
| CP-0430 | CO-0003-(BSB)-CP-0126 | 7.6 ± 0.1 | 6.7 ± 0.1 |
| CP-0431 | CO-0001-(BSD)-CP-0126 | 8.2 ± 0.1 | 6.3 ± 0.3 |
| CP-0432 | CO-0003-(BSD)-CP-0126 | 7.5 ± 0.2 | 6.1 ± 0.3 |

The BK antagonists of the invention, including both homo- and heterodimers, as well as the modified monomers, may be used in the form of conventional pharmaceutical compositions comprising the antagonist and a pharmaceutically acceptable carrier. Such compositions may be adapted for topical, oral, aerosolized, intramuscular, subcutaneous, or intravenous administration. The amount of antagonist present in such compositions will range from, for example, about 0.001 to 90.0% by weight depending on the application and mode of administration although more or less of the active component may be used. Conventional dosages will vary considerably on the basis of the intended application and mode of administration, e.g. 0.1 to 100 micrograms per kg body weight per minute are contemplated for use in the context of septic shock.

The scope of the invention is defined in the following claims wherein:

We claim:

1. A bradykinin antagonist of the formula:

$$BKA_1\text{-}X\text{-}BKA_2$$

wherein $BKA_1$ and $BKA_2$ are the same or different bradykinin antagonist peptides, X is a linking group, linking said peptides via the amino acid residue in the 0, 1, 2, 3, or 5 position of said peptides.

2. A bradykinin antagonist according to claim 1, wherein the linker X comprises one or more succinimido groups.

3. A bradykinin antagonist according to claim 2, wherein the peptide group (BKA) is covalently attached to the linker via a thioether bond.

4. A bradykinin antagonist according to claim 3, wherein the peptide group includes a cysteine residue; the linker comprises two succinimido groups and the succinimido group is liked to each peptide chain through the cysteine residue.

5. A bradykinin antagonist according to claim 4 wherein the linker is a bissuccinimidoalkane.

6. A bradykinin antagonist according to claim 5 wherein the bissuccinimidoalkane comprises an alkyl chain between 2 and 14 methylene groups in length.

7. A bradykinin antagonist according to claim 6 wherein the linking group has the formula:

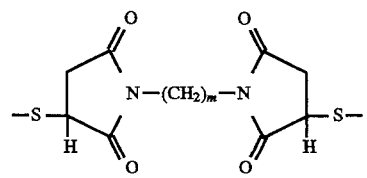

where m is 2–14.

8. A bradykinin antagonist according to claim 1, wherein the linking group is selected from the following:

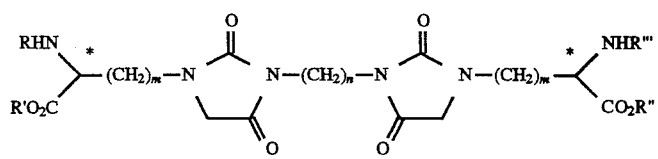

and

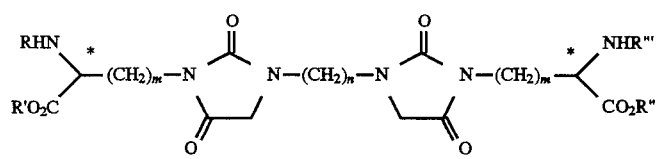

wherein m is 2–12 and n is 1–12, and R, R', R" and R'" are protecting groups.

9. A bradykinin antagonist of the formula:

X(BKA)

where BKA is the peptide chain of a bradykinin antagonist peptide and X is a modifying group linked to said peptide via the amino acid residue in the 0, 1, 2, 3 or 5 position of said peptide.

10. A bradykinin antagonist according to claim 9 wherein X is joined through the sulfhydryl group of a cysteine residue in the peptide chain BK.

11. A bradykinin antagonist according to claim 9 wherein X is an N-alkylsuccinimido group.

12. A bradykinin antagonist according to claim 9, wherein X is an N-alkylsuccinimido group with an alkyl chain consisting of 1 to 10 methylene groups.

* * * * *